United States Patent
Long et al.

(10) Patent No.: US 11,298,269 B2
(45) Date of Patent: *Apr. 12, 2022

(54) APPARATUS AND METHOD FOR MAKING SIDE SEAMS ON ABSORBENT ARTICLES

(71) Applicant: The Procter & Gamble Company, Cincinnati, OH (US)

(72) Inventors: Michael Devin Long, Springfield Township, OH (US); Kazuya Ogawa, Akashi (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/067,945

(22) Filed: Oct. 12, 2020

(65) Prior Publication Data

US 2021/0022926 A1    Jan. 28, 2021

Related U.S. Application Data

(63) Continuation of application No. 16/214,624, filed on Dec. 10, 2018, now Pat. No. 10,835,423, which is a
(Continued)

(51) Int. Cl.
*B29C 65/10* (2006.01)
*B32B 37/04* (2006.01)
(Continued)

(52) U.S. Cl.
CPC .. *A61F 13/15707* (2013.01); *A61F 13/15577* (2013.01); *A61F 13/15699* (2013.01);
(Continued)

(58) Field of Classification Search
CPC ................................................. A61F 13/49011
See application file for complete search history.

(56) References Cited

U.S. PATENT DOCUMENTS

| 3,860,003 A | 1/1975 | Buell |
| 4,610,678 A | 9/1986 | Weisman et al. |

(Continued)

FOREIGN PATENT DOCUMENTS

| JP | 2002355270 | 12/2002 |
| JP | 2013081769 | 5/2013 |

(Continued)

OTHER PUBLICATIONS

PCT International Search Report, dated Dec. 19, 2014, 8 pages.
All Office Actions for U.S. Appl. No. 14/492,114.
All Office Actions for U.S. Appl. No. 16/214,624.

*Primary Examiner* — Scott W Dodds
(74) *Attorney, Agent, or Firm* — Charles R. Matson

(57) ABSTRACT

The present disclosure relates to methods and apparatuses configured to bond elastic laminates together between a rotating drum and anvil. The drum includes a fluid nozzle and a press member. As such, a first elastic laminate and a second elastics laminate may be advanced in a machine direction onto the rotating drum. A fluid is heated to a temperature sufficient to partially melt substrate layers of the first and second elastic laminates. As the drum rotates, the press member shifts radially outward from the drum wherein a length, L, of the pattern surface extends in the cross direction across a plurality of elastic strands of first and/or second elastic laminates. And the partially melted portion of the substrate layers of the first and second elastic laminates and the plurality of elastic strands are then bonded together by being compressed between the pattern surface and the anvil roll.

10 Claims, 20 Drawing Sheets

Related U.S. Application Data continuation of application No. 14/492,114, filed on Sep. 22, 2014, now Pat. No. 10,172,745.

(60) Provisional application No. 61/881,003, filed on Sep. 23, 2013.

(51) Int. Cl.
*A61F 13/15* (2006.01)
*A61F 13/496* (2006.01)
*B29C 65/00* (2006.01)
*B29L 31/48* (2006.01)

(52) U.S. Cl.
CPC ...... *A61F 13/15747* (2013.01); *A61F 13/496* (2013.01); *B29C 65/10* (2013.01); *B29C 66/1122* (2013.01); *B29C 66/232* (2013.01); *B29C 66/43* (2013.01); *B29C 66/723* (2013.01); *B29C 66/73116* (2013.01); *B29C 66/81427* (2013.01); *B29C 66/81465* (2013.01); *B29C 66/82263* (2013.01); *B29C 66/8351* (2013.01); *B29C 66/83411* (2013.01); *B29C 66/83511* (2013.01); *B29C 66/83517* (2013.01); *B29C 66/71* (2013.01); *B29C 66/729* (2013.01); *B29C 66/7294* (2013.01); *B29C 66/72343* (2013.01); *B29C 66/73161* (2013.01); *B29C 66/8167* (2013.01); *B29C 66/83415* (2013.01); *B29C 66/91933* (2013.01); *B29C 66/91935* (2013.01); *B29C 66/929* (2013.01); *B29C 66/949* (2013.01); *B29L 2031/4878* (2013.01)

(56) References Cited

U.S. PATENT DOCUMENTS

| | | |
|---|---|---|
| 4,630,320 A | 12/1986 | Van Gompel |
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,888,231 A | 12/1989 | Angstadt |
| 4,909,803 A | 3/1990 | Aziz et al. |
| 5,562,646 A | 10/1996 | Goldman et al. |
| 5,599,335 A | 2/1997 | Goldman et al. |
| 5,628,097 A | 5/1997 | Benson et al. |
| 5,643,396 A | 7/1997 | Rajala et al. |
| 5,669,894 A | 9/1997 | Goldman et al. |
| 5,772,825 A | 6/1998 | Schmitz |
| 5,916,661 A | 6/1999 | Benson et al. |
| 6,107,539 A | 8/2000 | Palumbo et al. |
| 6,248,195 B1 | 6/2001 | Schmitz |
| 6,545,197 B1 | 4/2003 | Muller et al. |
| 6,790,798 B1 | 9/2004 | Suzuki et al. |
| 7,059,103 B2 | 6/2006 | Ninomiya et al. |
| 7,569,039 B2 | 8/2009 | Matsuda et al. |
| 7,587,966 B2 | 9/2009 | Nakakado et al. |
| 8,029,631 B2 | 10/2011 | Cartier et al. |
| 8,440,043 B1 | 5/2013 | Schneider et al. |
| 8,607,959 B2 | 12/2013 | Papsdorf et al. |
| 8,720,666 B2 | 5/2014 | Papsdorf et al. |
| 8,778,127 B2 | 7/2014 | Schneider |
| 2002/0092604 A1 | 7/2002 | McCabe et al. |
| 2004/0097895 A1 | 5/2004 | Busam et al. |
| 2004/0106506 A1 | 6/2004 | Ninomiya et al. |
| 2004/0158212 A1 | 8/2004 | Ponomarenko et al. |
| 2009/0312730 A1 | 12/2009 | LaVon et al. |
| 2012/0021186 A1 | 1/2012 | Schneider |
| 2012/0061015 A1 | 3/2012 | LaVon et al. |
| 2012/0061016 A1 | 3/2012 | LaVon et al. |
| 2012/0065043 A1 | 3/2012 | Lam et al. |
| 2012/0157281 A1 | 6/2012 | Schneider et al. |
| 2013/0138072 A1 | 5/2013 | Morimoto |
| 2013/0213547 A1 | 8/2013 | Schneider et al. |
| 2013/0218116 A1 | 8/2013 | Schneider et al. |
| 2013/0255861 A1 | 10/2013 | Schneider |
| 2013/0255862 A1 | 10/2013 | Schneider et al. |
| 2013/0255863 A1 | 10/2013 | Schneider et al. |
| 2013/0255864 A1 | 10/2013 | LaVon et al. |
| 2013/0255865 A1 | 10/2013 | Dean et al. |
| 2013/0270065 A1 | 10/2013 | Papsdorf et al. |
| 2013/0270066 A1 | 10/2013 | Papsdorf et al. |
| 2013/0304011 A1 | 11/2013 | Sasayama et al. |
| 2015/0083309 A1 | 3/2015 | Long |
| 2019/0105205 A1 | 4/2019 | Long et al. |

FOREIGN PATENT DOCUMENTS

| | | |
|---|---|---|
| JP | 2013094420 | 5/2013 |
| WO | 9619123 A1 | 6/1996 |
| WO | WO 2011156299 | 12/2011 |
| WO | WO 2013119484 | 8/2013 |

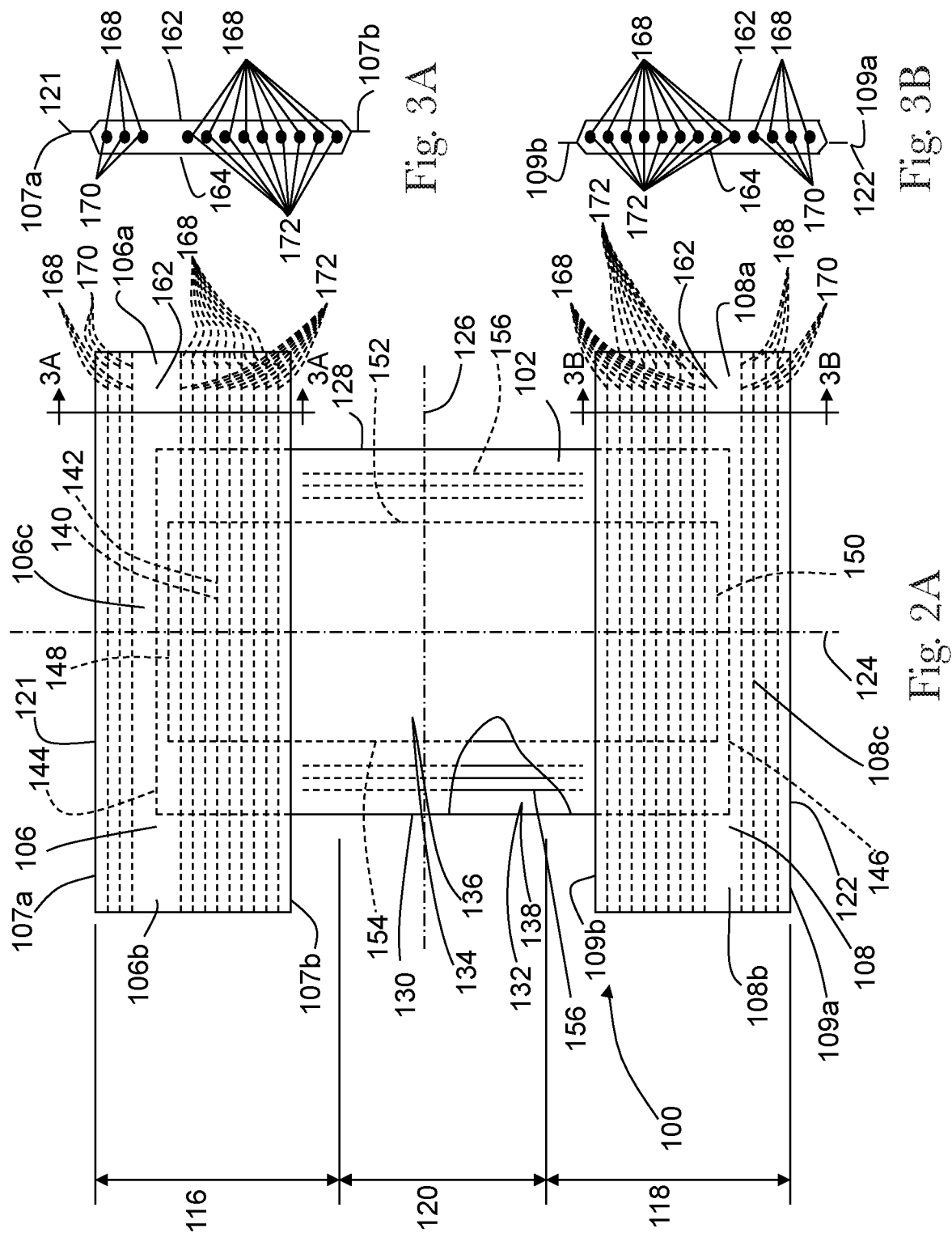

Fig. 4

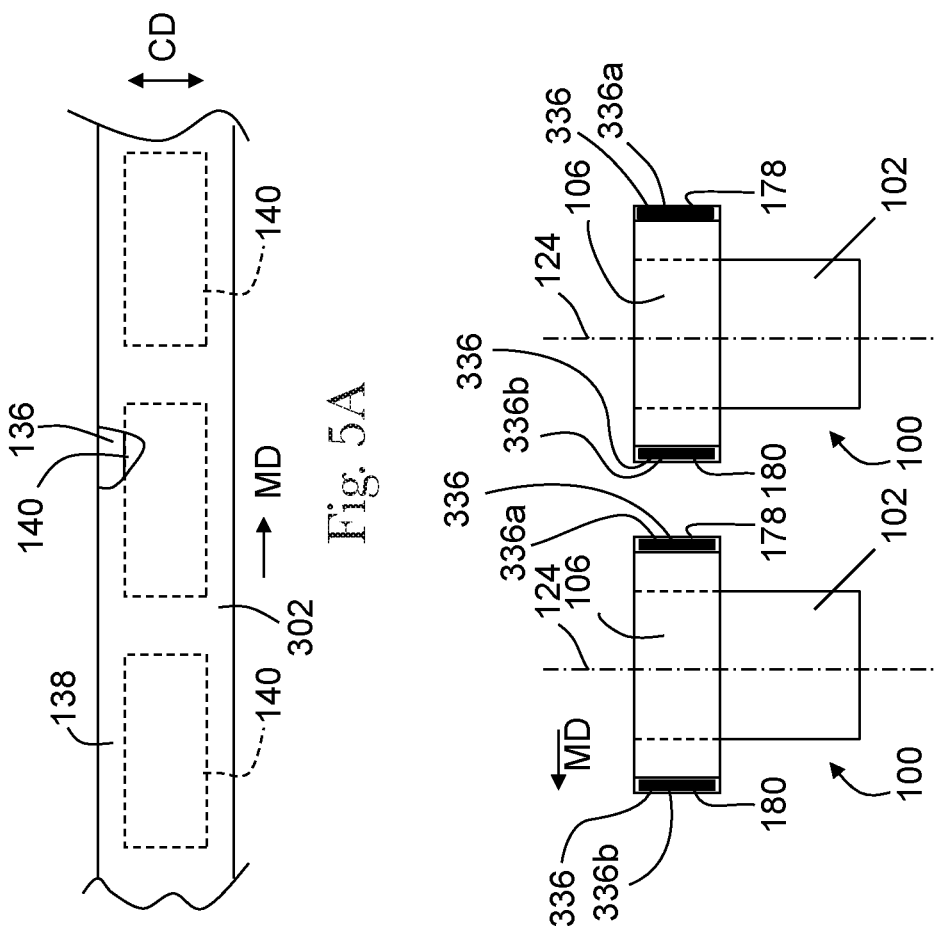

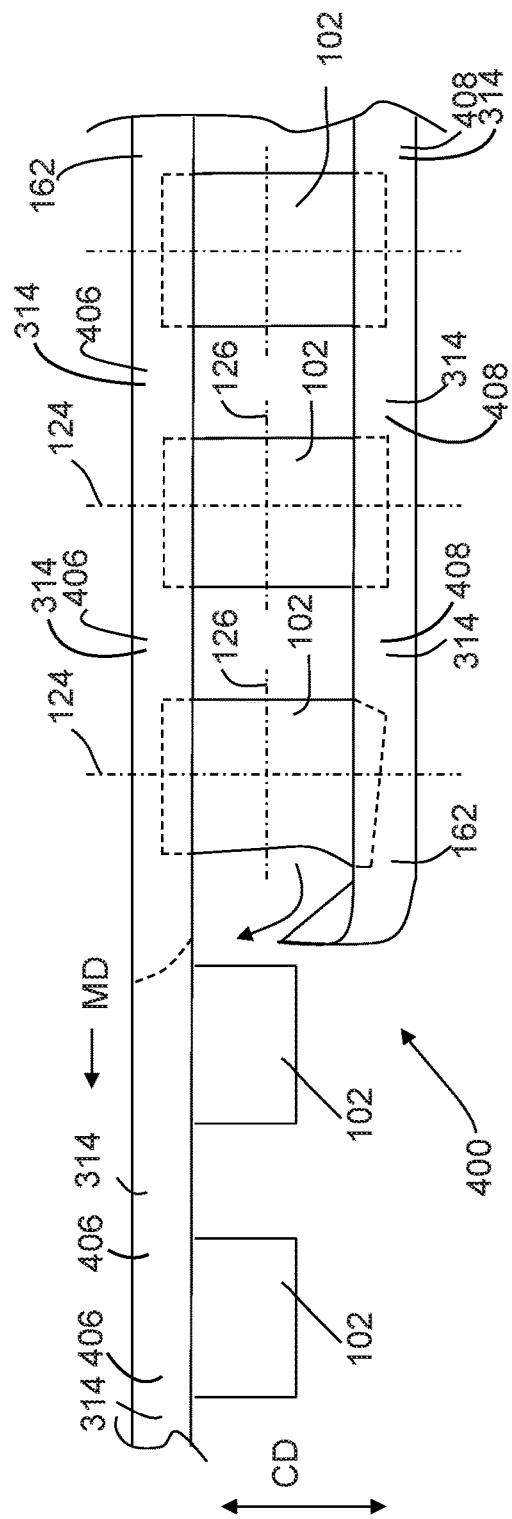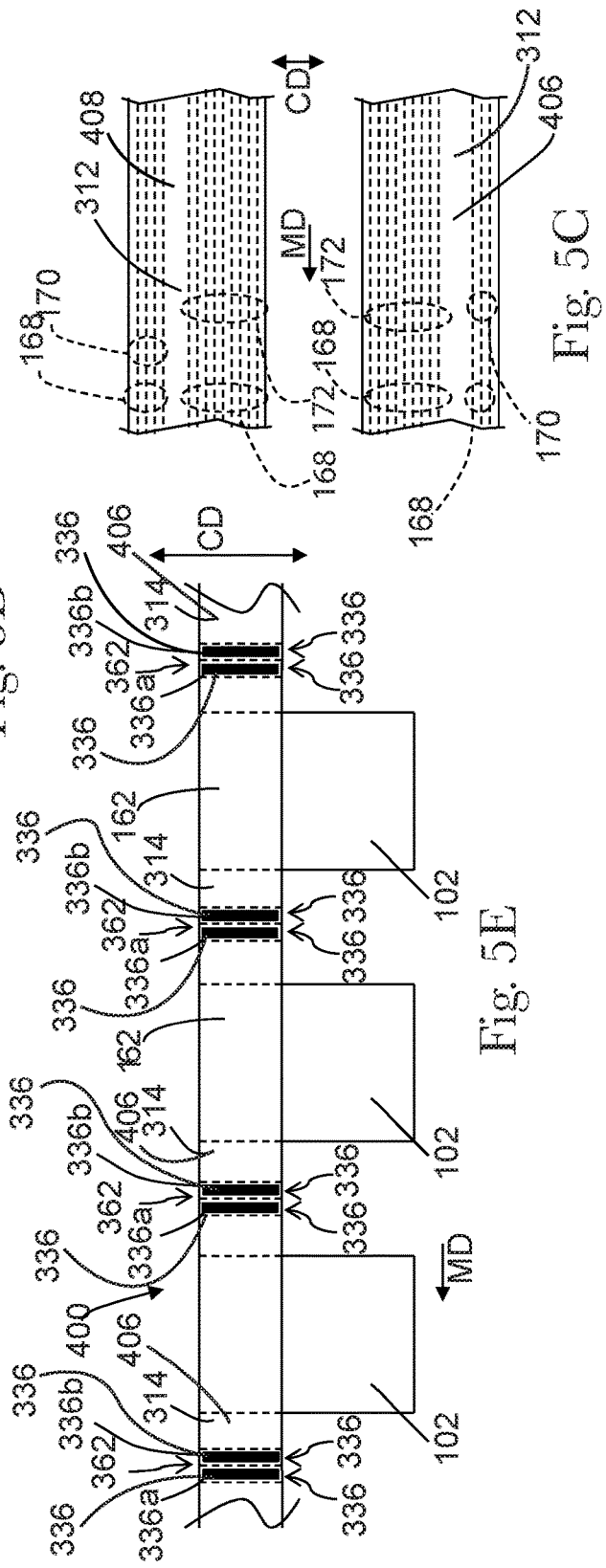

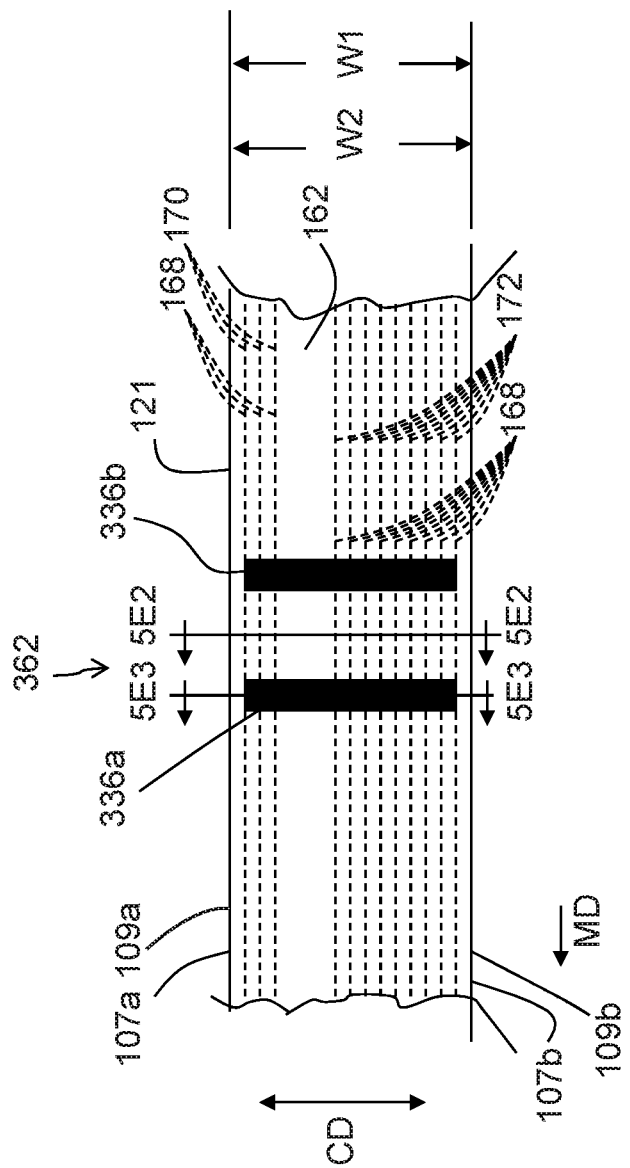

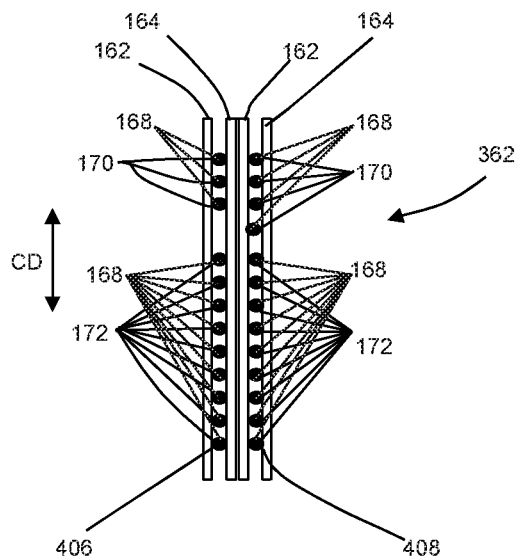
Fig. 5E2
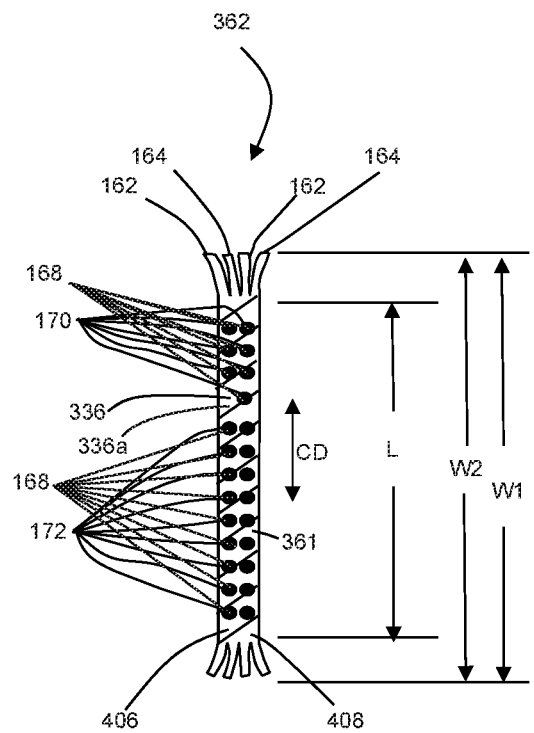
Fig. 5E3A

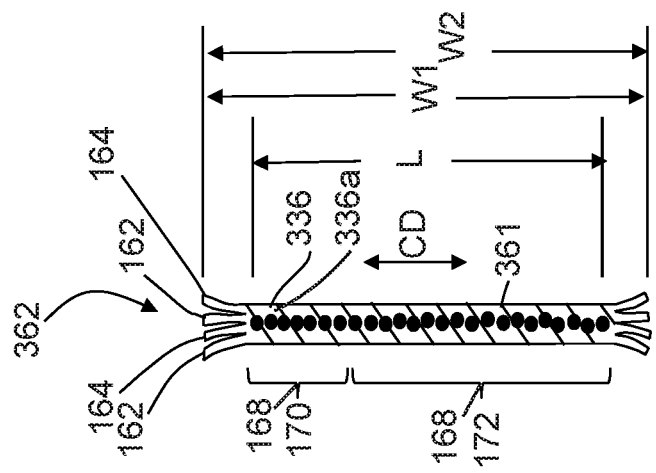
Fig. 5E3C
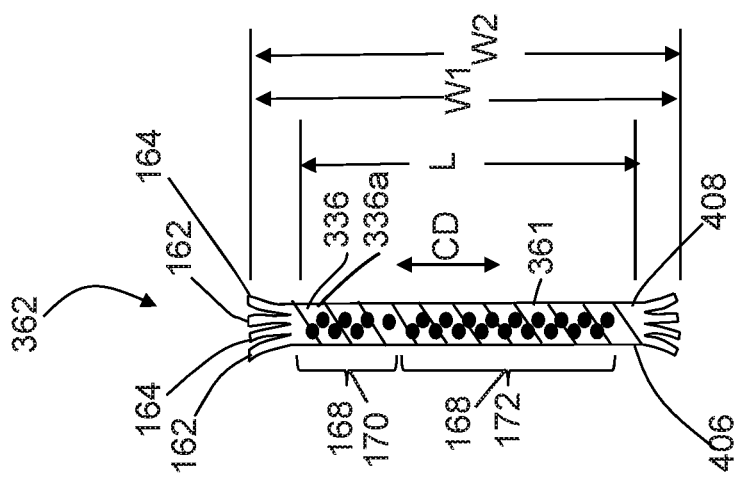
Fig. 5E3B

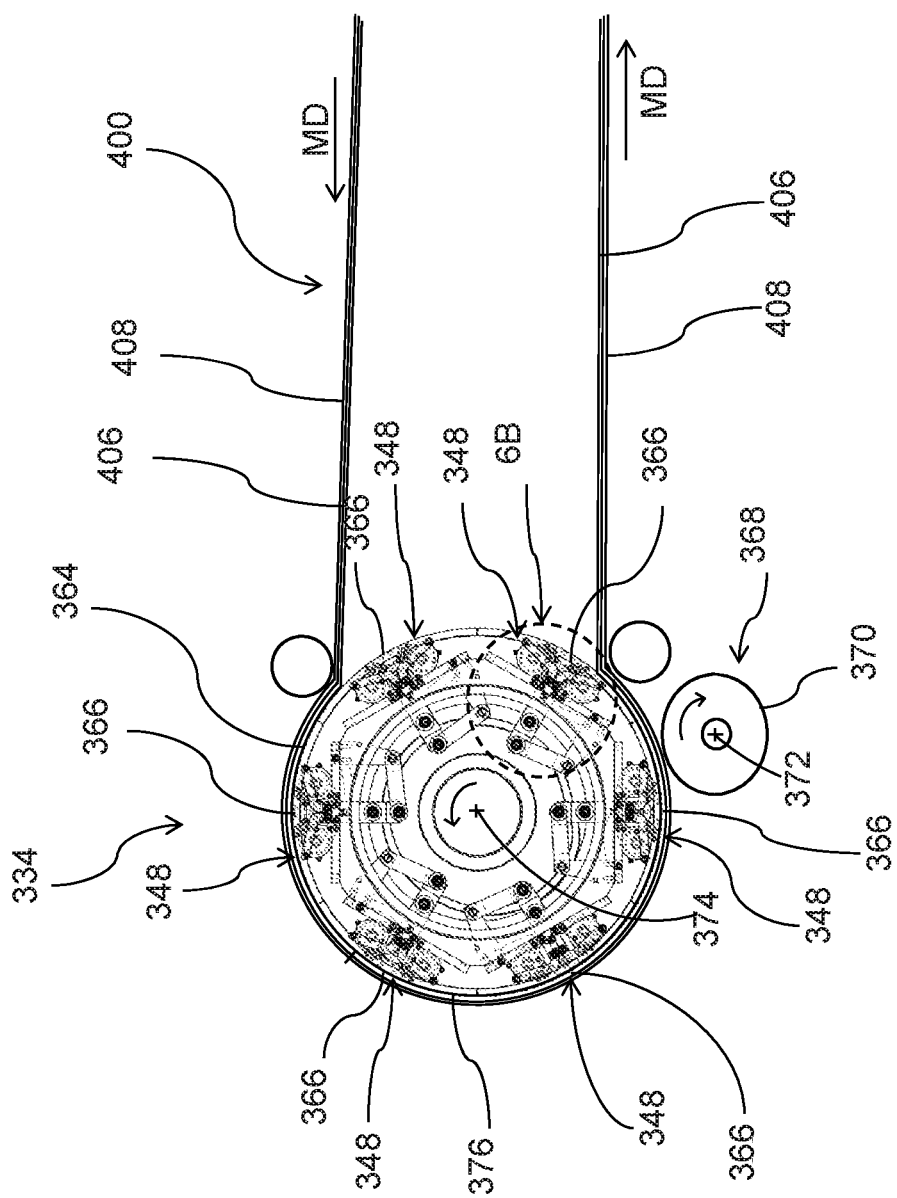

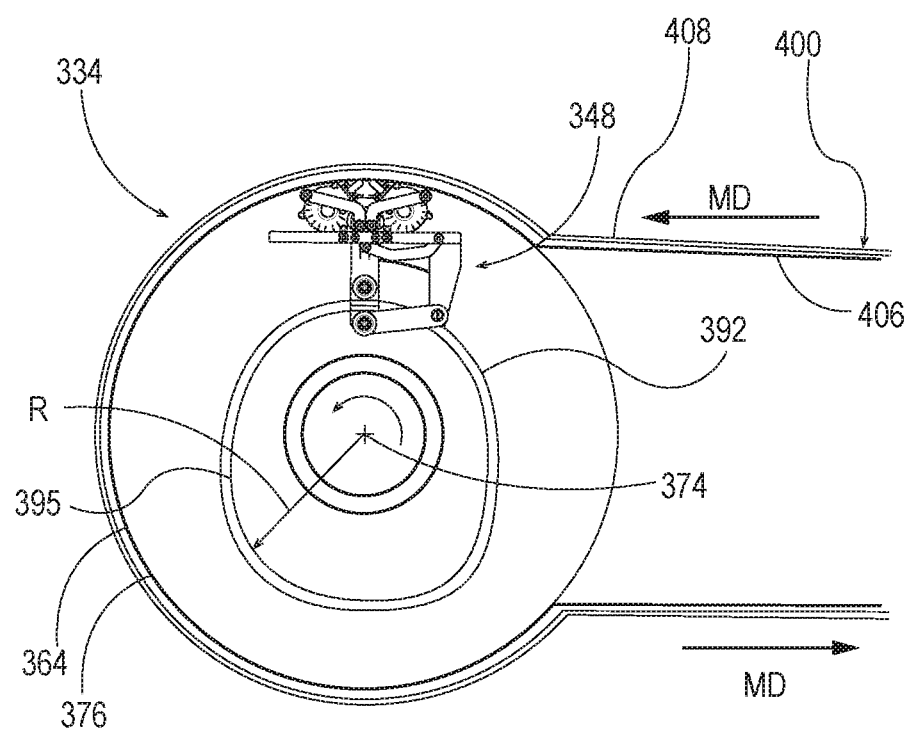
Fig. 6A1

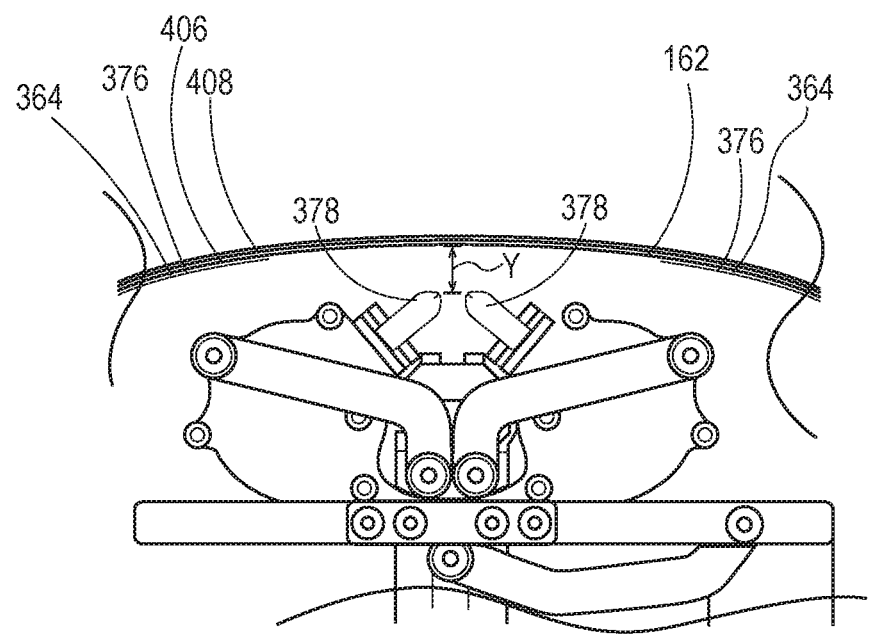
Fig. 6B1

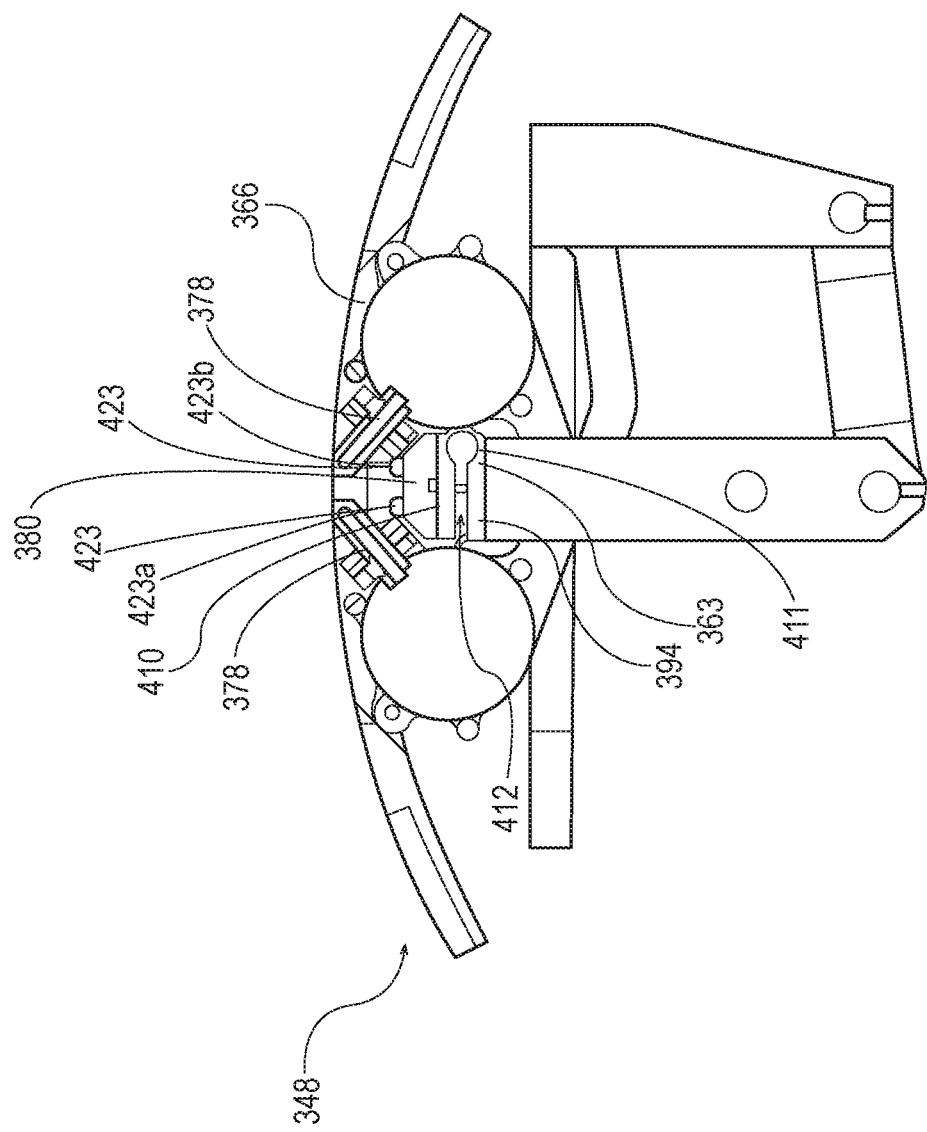

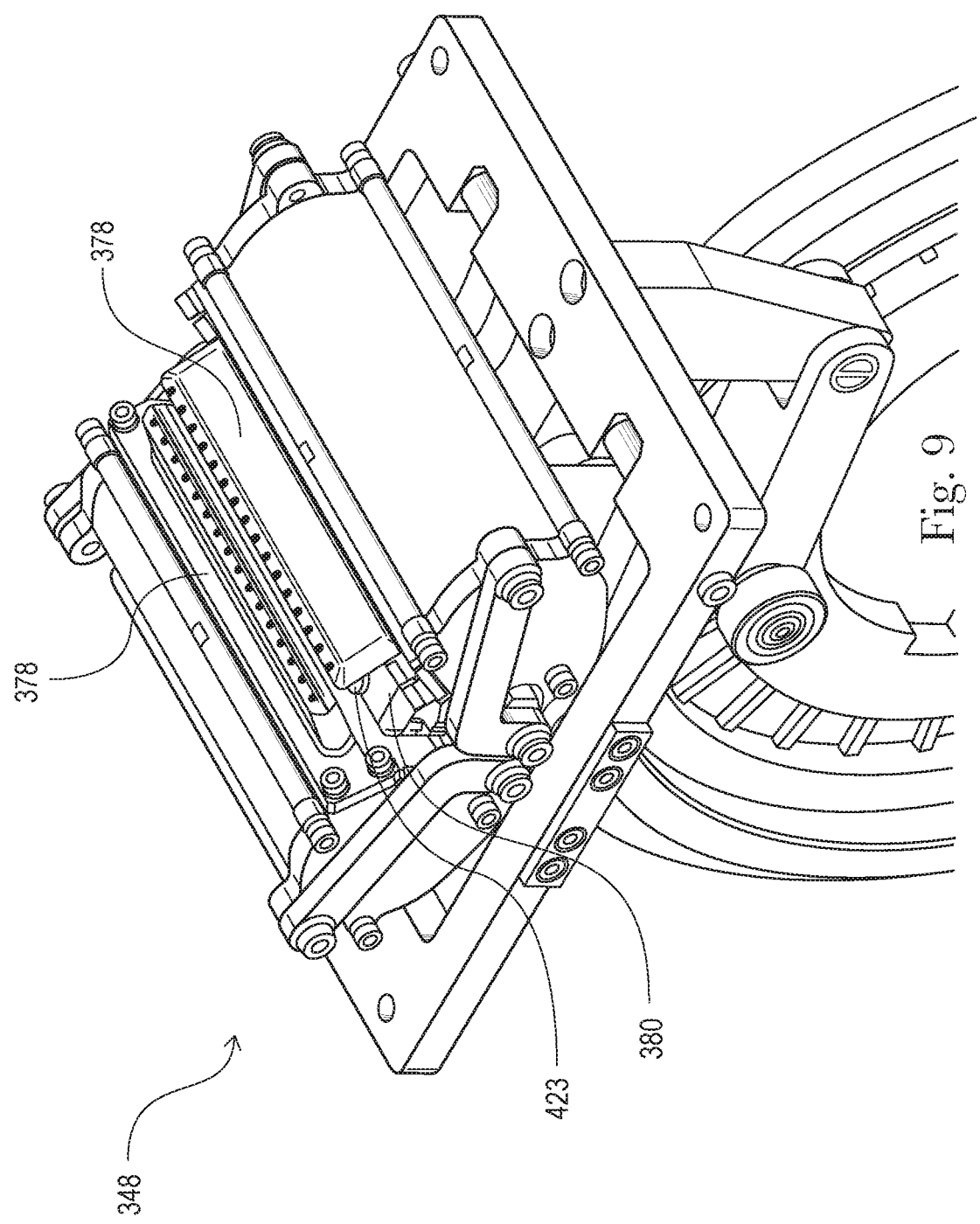

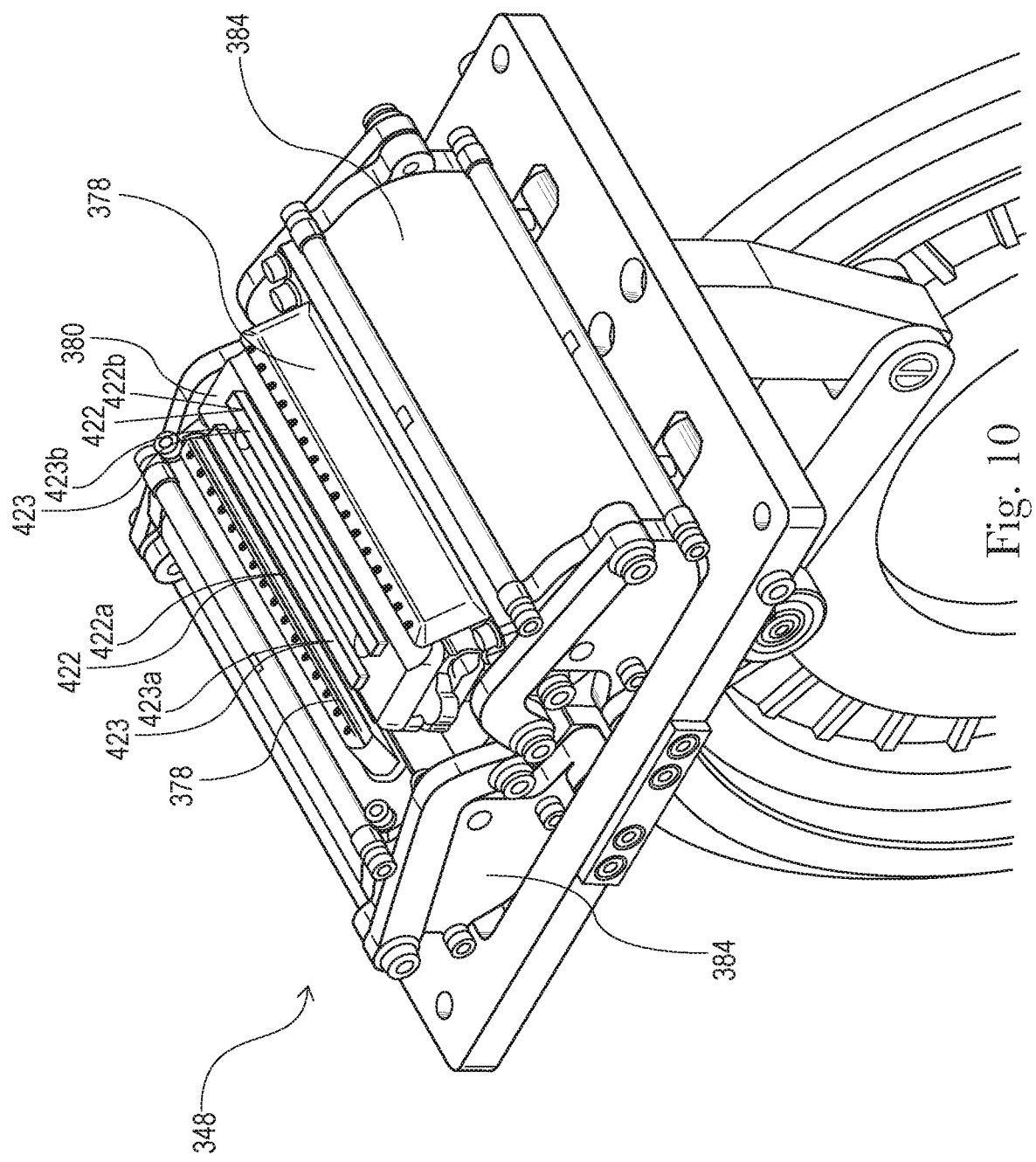

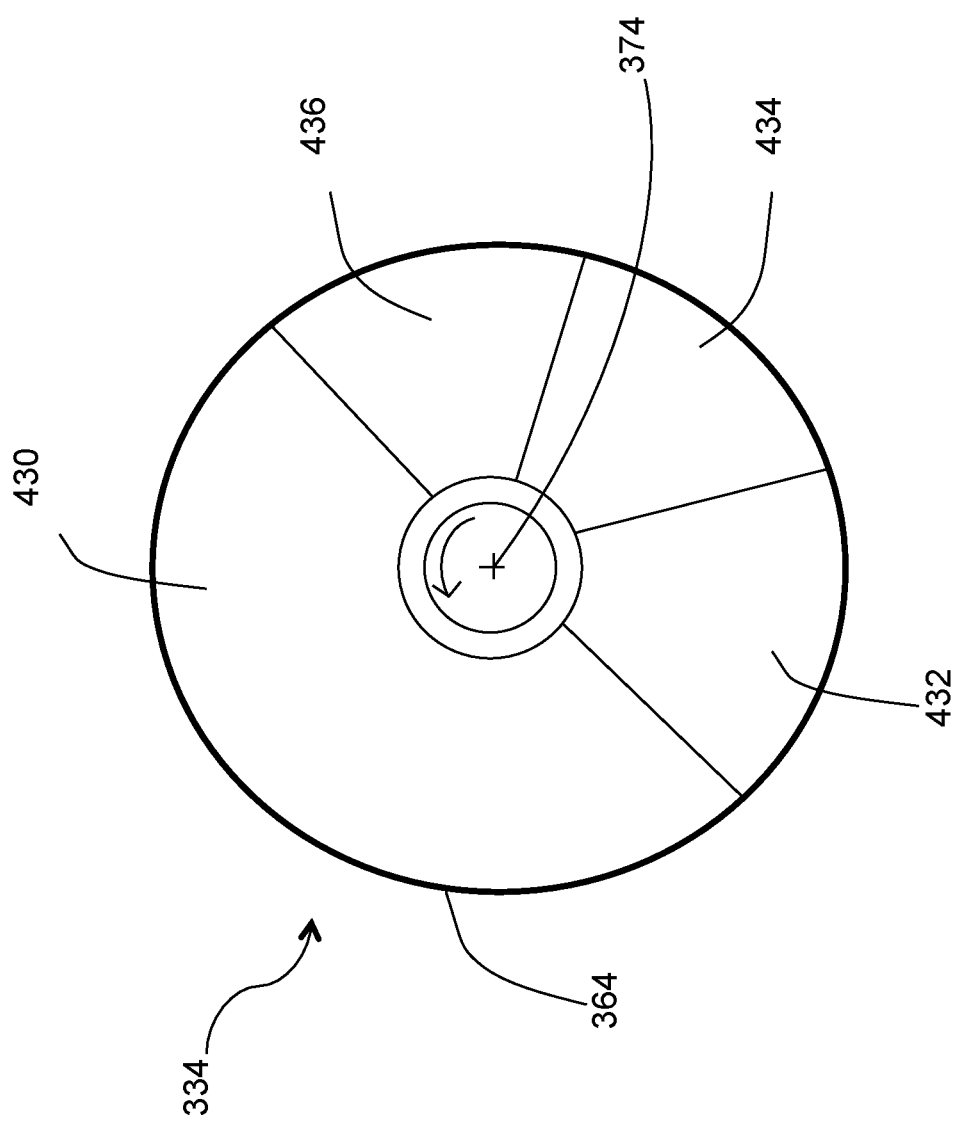

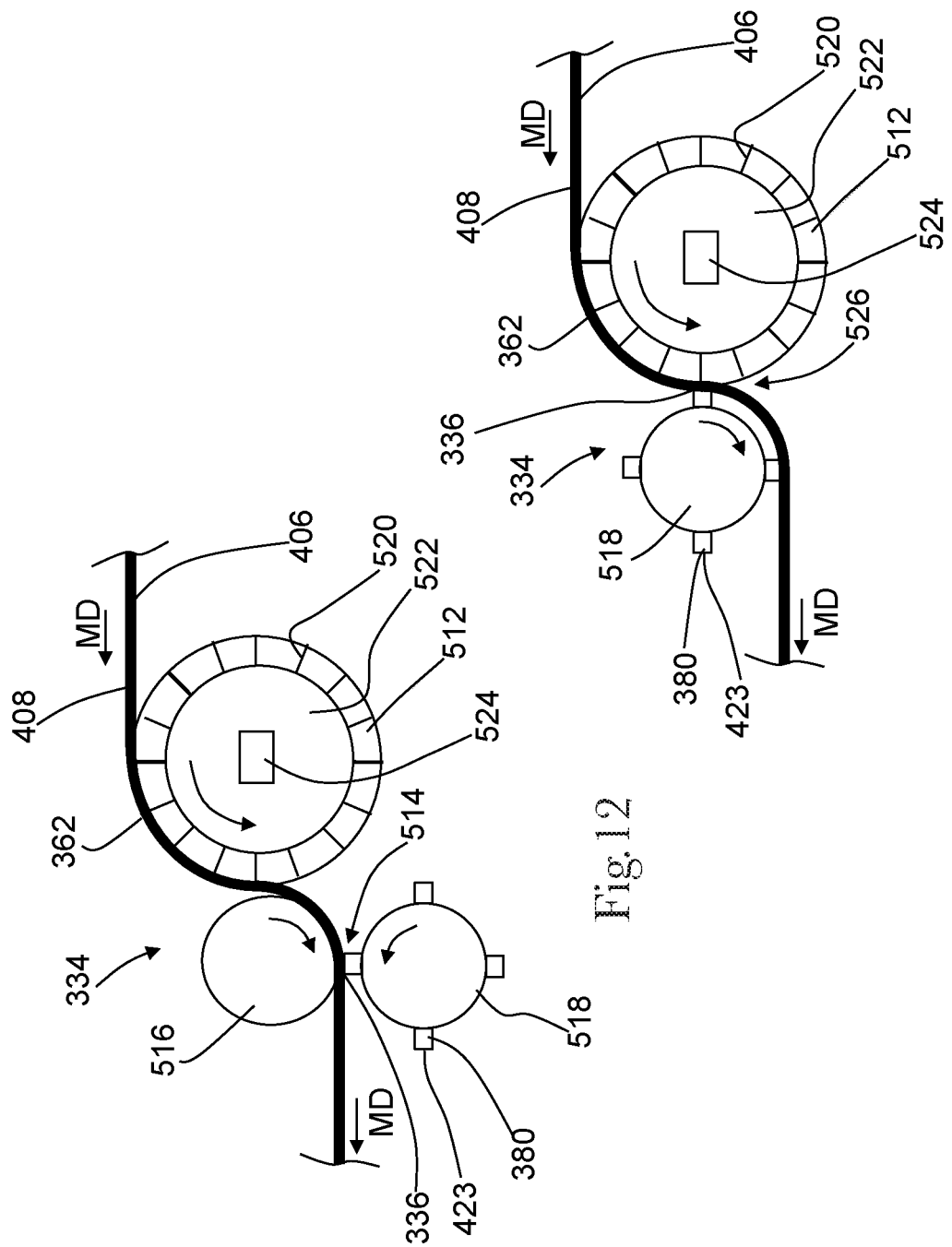

APPARATUS AND METHOD FOR MAKING SIDE SEAMS ON ABSORBENT ARTICLES

CROSS REFERENCE TO RELATED APPLICATIONS

This application is a continuation of U.S. application Ser. No. 16/214,624, filed on Dec. 10, 2018, which is a continuation of U.S. application Ser. No. 14/492,114, filed on Sep. 22, 2014, which claims the benefit of U.S. Provisional Application No. 61/881,003, filed on Sep. 23, 2013, all of which are incorporated herein by reference.

FIELD OF THE INVENTION

The present disclosure relates to methods for manufacturing absorbent articles, and more particularly, to apparatuses and methods for bonding elastic laminates that may be used as components of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

During the assembly process, various components and/or advancing webs of material may be bonded together in various ways. For example, advancing webs and/or components may be bonded together to create side seams on diapers. In some processes, advancing webs and/or components may be bonded with adhesives and/or with ultrasonic bonding apparatuses. In other processes, advancing webs and/or components may be mechanically bonded together with heat and pressure with or without the use of adhesives. In yet other processes, portions of advancing webs may be partially melted with hot air and then pressed together with a press member, wherein the press member includes a plurality of relatively small discrete pattern elements. Thus, each side seam created with such hot air seaming processes includes a plurality of discrete, relatively small, bond sites arranged along the length of each side seam. However, some present apparatuses and processes used to create side seams with pluralities of discrete bonds may have certain disadvantages. For example, some material from the melted portions of the substrates may tend to collect on the pattern elements, causing degraded qualities of bonds and necessitating relatively frequent cleanings. In addition, some diaper embodiments may include elastic belts including elastic strands sandwiched between substrates. When bonding the elastic belts together to create side seams, substrate material may not be adhered to the elastic strands. Thus, some elastic strands may tend retract or snap back from the sides seams after the final knife cut.

Consequently, it would be beneficial to provide a method and apparatus for utilizing hot air seaming methods to bond substrates that are configured to help reduce the need for frequent cleaning and/or to help reduce the occasions of elastic strand snap back from side seams.

SUMMARY OF THE INVENTION

The present disclosure relates to methods and apparatuses configured to bond elastic laminates together between a rotating drum and anvil. The drum includes a fluid nozzle and a press member. As such, a first elastic laminate and a second elastics laminate may be advanced in a machine direction onto the rotating drum. A fluid is heated to a temperature sufficient to partially melt substrate layers of the first and second elastic laminates. As the drum rotates, the press member shifts radially outward from the drum wherein a length, L, of the pattern surface extends in the cross direction across a plurality of elastic strands of first and/or second elastic laminates. And the partially melted portion of the substrate layers of the first and second elastic laminates and the plurality of elastic strands are then bonded together by being compressed between the pattern surface and the anvil roll.

In one form, a method for assembling disposable pant diapers, wherein each pant diaper includes a chassis having a first end region and an opposing second end region separated from each other by a central region, and having a longitudinal axis and a lateral axis, the chassis comprising: a topsheet, a backsheet, and an absorbent core disposed between the topsheet and the backsheet, comprises the steps of: advancing a continuous first substrate layer in a machine direction; advancing a continuous second substrate layer in the machine direction; stretching a plurality of elastic strands in the machine direction; adhering the stretched plurality of elastic strands between the first substrate layer and the second substrate layer to form a continuous elastic laminate; rotating a drum about an axis of rotation, the drum comprising a fluid nozzle and a press member, wherein the press member comprises a pattern surface that defines a length, L, that extends in a cross direction; rotating an anvil roll adjacent the drum; advancing the elastic laminate on the drum, wherein the first substrate layer is between the stretched plurality of elastic strands and the drum, and wherein the stretched plurality of elastic strands are between the first substrate layer and the second substrate layer; heating a fluid to a temperature sufficient to partially melt the first substrate layer and the second substrate layer; moving the fluid nozzle radially outward from the drum; partially melting a portion of the first substrate layer and a portion of the second substrate layer by directing a jet of the heated fluid onto the first substrate layer and second substrate layer; retracting the fluid nozzle radially inward into the drum; shifting the press member radially outward from the drum such that the length, L, of the pattern surface extends across the plurality of stretched elastic strands; and bonding the first substrate layer, the stretch plurality of elastic strands, and the second substrate layer together by compressing the partially melted portion of the first substrate layer, the stretched plurality of elastic strands, and the partially melted portion of the second substrate layer between the pattern surface and the anvil roll.

In another form, a method for assembling disposable pant diapers, wherein each pant diaper includes a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method includes the steps of: advancing a continuous first elastic laminate a machine direction, the first elastic laminate comprising a plurality of elastic strands extending between a first substrate layer and a second substrate layer; advancing a continuous second elastic laminate a machine direction, the first elastic laminate comprising a plurality of elastic strands extending between a first substrate layer and a second substrate layer; rotating a drum about an axis of rotation, the drum comprising a fluid nozzle and a press member, wherein the press member comprises a pattern surface that defines a length that extends in a cross direction; rotating an anvil roll adjacent the drum; advancing the first elastic laminate and the second elastic laminate on the drum, wherein the first elastic laminate is between the second elastic laminate and the drum; heating a fluid to a temperature sufficient to partially melt the first substrate layer and the second substrate layer of the first elastic laminate and the second elastic laminate; moving the fluid nozzle radially outward from the drum; partially melting a portion of the first substrate layer and a portion of the second substrate layer of the first elastic laminate and the second elastic laminate by directing a jet of the heated fluid onto the first elastic laminate and the second the elastic laminate; retracting the fluid nozzle radially inward into the drum; shifting the press member radially outward from the drum wherein the length, L, of the pattern surface extends across the plurality of elastic strands of first elastic laminate or the second elastic laminate; and compressing the partially melted portion of the first substrate layer, the stretched plurality of elastic strands, and the partially melted portion of the second substrate layer of the first elastic laminate and the second elastic laminate between the pattern surface and the anvil roll.

In yet another form, a method for bonding an elastic laminate includes the steps of: advancing a continuous first substrate layer in a machine direction; advancing a continuous second substrate layer in the machine direction; extending a plurality of elastic strands between the first substrate layer and the second substrate layer to form a continuous elastic laminate; advancing the elastic laminate on the drum, wherein the first substrate layer is between the plurality of elastic strands and the drum, and wherein the plurality of elastic strands are between the first substrate layer and the second substrate layer; heating a fluid to a temperature sufficient to partially melt the first substrate layer and the second substrate layer; partially melting a portion of the first substrate layer and a portion of the second substrate layer by directing a jet of the heated fluid onto the first substrate layer and second substrate layer; positioning a press member adjacent the first substrate layer, wherein the press member comprises a pattern surface that defines a length, L, that extends in a cross direction and wherein the length of the pattern surface extends across the plurality of elastic strands; and compressing the partially melted portion of the first substrate layer, the plurality of elastic strands, and the partially melted portion of the second substrate layer between the pattern surface and an anvil.

BRIEF DESCRIPTION OF THE DRAWINGS

FIG. 2A is a partially cut away plan view of the diaper pant shown in FIG. 1.
FIG. 3A is a cross-sectional view of the diaper pants of FIGS. 2A and 2B taken along line 3A-3A.
FIG. 3B is a cross-sectional view of the diaper pants of FIGS. 2A and 2B taken along line 3B-3B.
FIG. 4 is a schematic side view of a converting apparatus adapted to manufacture pre-fastened, pant diapers.
FIG. 5A is a view of a continuous length of chassis assemblies from FIG. 4 taken along line A-A.
FIG. 5B1 is a view of a discrete chassis from FIG. 4 taken along line B1-B1.
FIG. 5B2 is a view of a discrete chassis from FIG. 4 taken along line B2-B2.
FIG. 5C is a view of continuous lengths of advancing front and back side panel material from FIG. 4 taken along line C-C.
FIG. 5D is a view of multiple discrete chassis spaced from each other along the machine direction MD and connected with each other by the front and back side panel material from FIG. 4 taken along line D-D.
FIG. 5E is a view of folded multiple discrete chassis with the front and back side panel material in a facing relationship from FIG. 4 taken along line E-E.
FIG. 5E1 is a detailed view of a bonded overlapped area from FIG. 5E.
FIG. 5E2 is a cross-sectional view of the overlapped area between two bonds from FIG. 5E1 taken along line 5E2-5E2.
FIG. 5E3A is a cross-sectional view of a first embodiment of a bond from FIG. 5E1 taken along line 5E3-5E3.
FIG. 5E3B is a cross-sectional view of a second embodiment of a bond from FIG. 5E1 taken along line 5E3-5E3.
FIG. 5E3C is a cross-sectional view of a third embodiment of a bond from FIG. 5E1 taken along line 5E3-5E3.
FIG. 5F is a view of two discrete absorbent articles advancing the machine direction MD from FIG. 4 taken along line F-F.
FIG. 6A is a schematic side view of a bonder apparatus adapted to seam pre-fastened pant diapers.
FIG. 6A1 is a detailed, schematic side view of the bonder apparatus of FIG. 6A.
FIG. 6B1 is a detailed elevation view of the seamer station of FIG. 6B.
FIG. 8 is an elevation view of an embodiment of a seaming station.
FIG. 9 is a perspective view of an embodiment of a seaming station in a first configuration.
FIG. 10 is a perspective view of an embodiment of a seaming station in a second configuration.
FIG. 11 is a schematic view of a bonder apparatus demonstrating the various configurations of a seaming station around a drum.
FIG. 12 is a schematic side view of a second embodiment of a bonder apparatus.
FIG. 13 is a schematic side view of a third embodiment of a bonder apparatus.

DETAILED DESCRIPTION OF THE INVENTION

Figure 1:
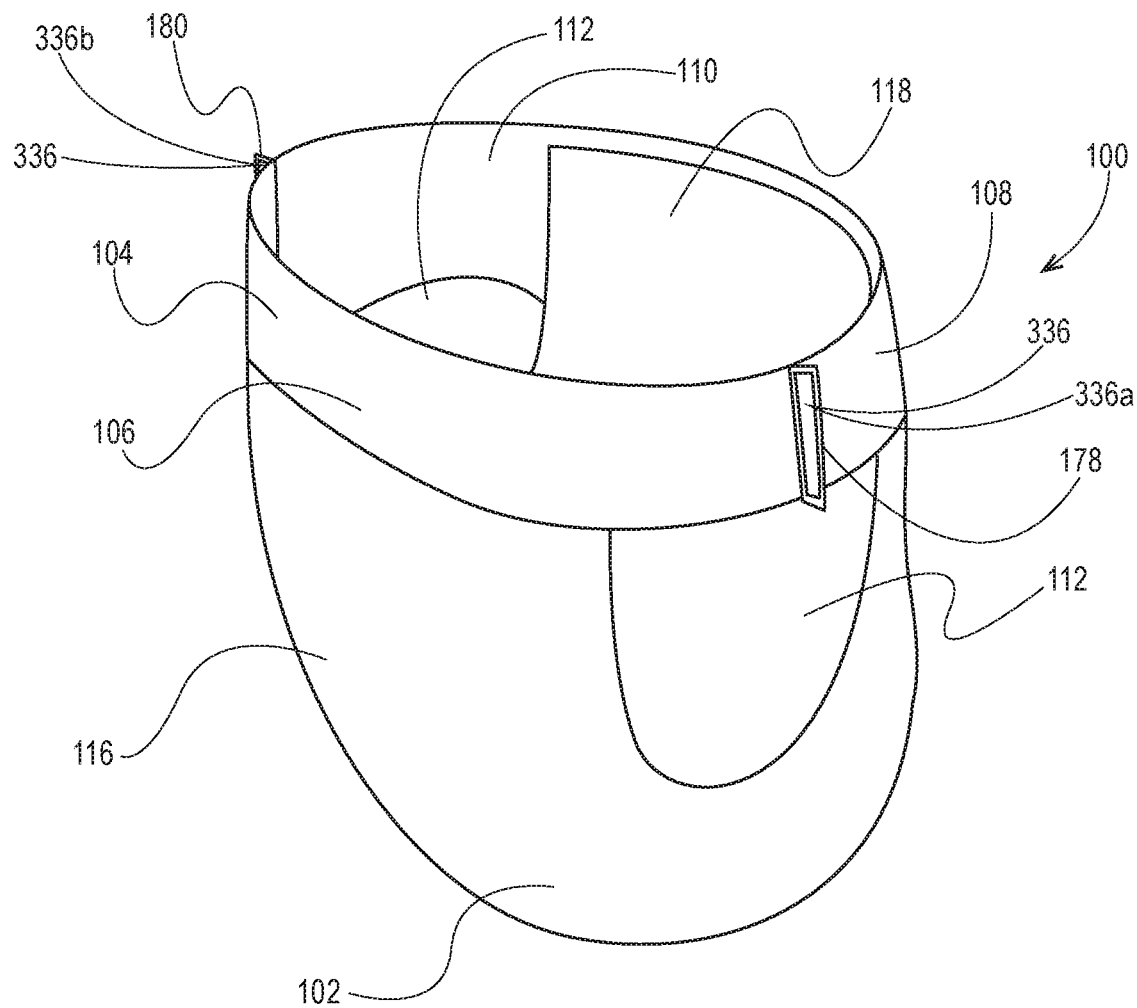
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Radial" means a direction running from the center of a drum toward a drum outer circumferential surface.

The term "substrate" is used herein to describe a material which is primarily two-dimensional (i.e. in an XY plane) and whose thickness (in a Z direction) is relatively small (i.e. $\frac{1}{10}$ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

The present disclosure relates to methods and apparatuses for manufacturing absorbent articles, and in particular, to methods and apparatuses for bonding elastic laminates together when assembling absorbent articles. As discussed below in more detail below, the methods and apparatuses herein may be configured to bond elastic laminates together between a rotating drum and anvil. The drum includes a fluid nozzle and a press member, wherein the press member includes a pattern surface that defines a length that extends in a cross direction. As such, a first elastic laminate and a second elastics laminate may be advanced in a machine direction onto the rotating drum. Each elastic laminate may include a plurality of elastic strands extending between a first substrate layer and a second substrate layer. The first elastic laminate may be positioned between the second elastic laminate and the drum. A fluid is heated to a temperature sufficient to partially melt the first substrate layer and the second substrate layer of the first and second elastic laminates. As the drum rotates, the fluid nozzle moves radially outward from the drum and directs a jet of the heated fluid onto the first and second elastic laminates to partially melt a portion of the first substrate layer and a portion of the second substrate layer of each elastic laminate. The fluid nozzle then radially retracts inward into the drum, and the press member shifts radially outward from the drum wherein a length, L, of the pattern surface extends in the cross direction across the plurality of elastic strands of first elastic laminate or the second elastic laminate. The partially melted portion of the first substrate layer, the stretched plurality of elastic strands, and the partially melted portion of the second substrate layer of the first and second elastic laminates are then bonded together by being compressed between the pattern surface and the anvil roll. As discussed in more detail below in the context of assembling pant diapers, the elastic laminates may be configured as front and back belts, and wherein the methods and apparatuses are used to bond the front and back belts together between a drum and an anvil to form side seams.

The press member herein may not have a plurality of discrete pattern surfaces. Rather, the pattern surface defines a length, L, that extends in the cross direction. As such, the pattern surface may be configured to create a single, contiguous bond extending a length, L, extending in the cross direction across the elastic laminate. In some configurations, wherein the continuous elastic laminate defines a maximum width, W, extending in the cross direction, and the length, L, of the pattern surface is at least 30% of W. As previously mentioned, the elastic laminate may include elastic strands sandwiched between first and second substrate layers, extending in the machine direction, and spaced apart from each other along the cross direction. As such, the pattern surface may extend across a plurality of elastic strands. Thus, when compressing the elastic laminate with the pattern surface, partially melted portions of the first and second substrate layers are bonded with each other as well as the elastic strands. As discussed in more detail below, bonding the substrate layers with the elastic strands helps to hold the strands in the bonded region, such as the side seams of diapers. Also, because the press member herein may not include a plurality of discrete, relatively small pattern surfaces, melted material from the bonded substrate layers is less likely to gather and/or build-up on the press member. Thus, the press member herein may require relatively less frequent cleanings and/or replacement.

As previously mentioned, the processes and apparatuses discussed herein may be used to bond various types of substrate configurations, some of which may be used in the manufacture of different types of absorbent articles. To help provide additional context to the subsequent discussion of the process embodiments, the following provides a general description of absorbent articles in the form of diapers that include components that may be bonded in accordance with the methods and apparatuses disclosed herein.

FIGS. 1 and 2A show an example of a diaper pant 100 that may be assembled and folded in accordance with the apparatuses and methods disclosed herein. In particular, FIG. 1 shows a perspective view of a diaper pant 100 in a pre-fastened configuration, and FIG. 2A shows a plan view of the diaper pant 100 with the portion of the diaper that faces away from a wearer oriented toward the viewer. The diaper pant 100 shown in FIGS. 1 and 2A includes a chassis 102 and a ring-like elastic belt 104. As discussed below in more detail, a first elastic belt 106 and a second elastic belt 108 are bonded together to form the ring-like elastic belt 104.

With continued reference to FIG. 2A, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2A are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 140 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; and U.S. Patent Publication No. 2009/0312730 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 116 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 107b may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172. As shown in FIG. 2A, the elastic strands 168 continuously extend laterally between the first and second opposing end regions 106a, 106b of the first elastic belt 106 and between the first and second opposing end regions 108a, 108b of the second elastic belt 108. In some embodiments, some elastic strands 168 may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

Figure 2B:
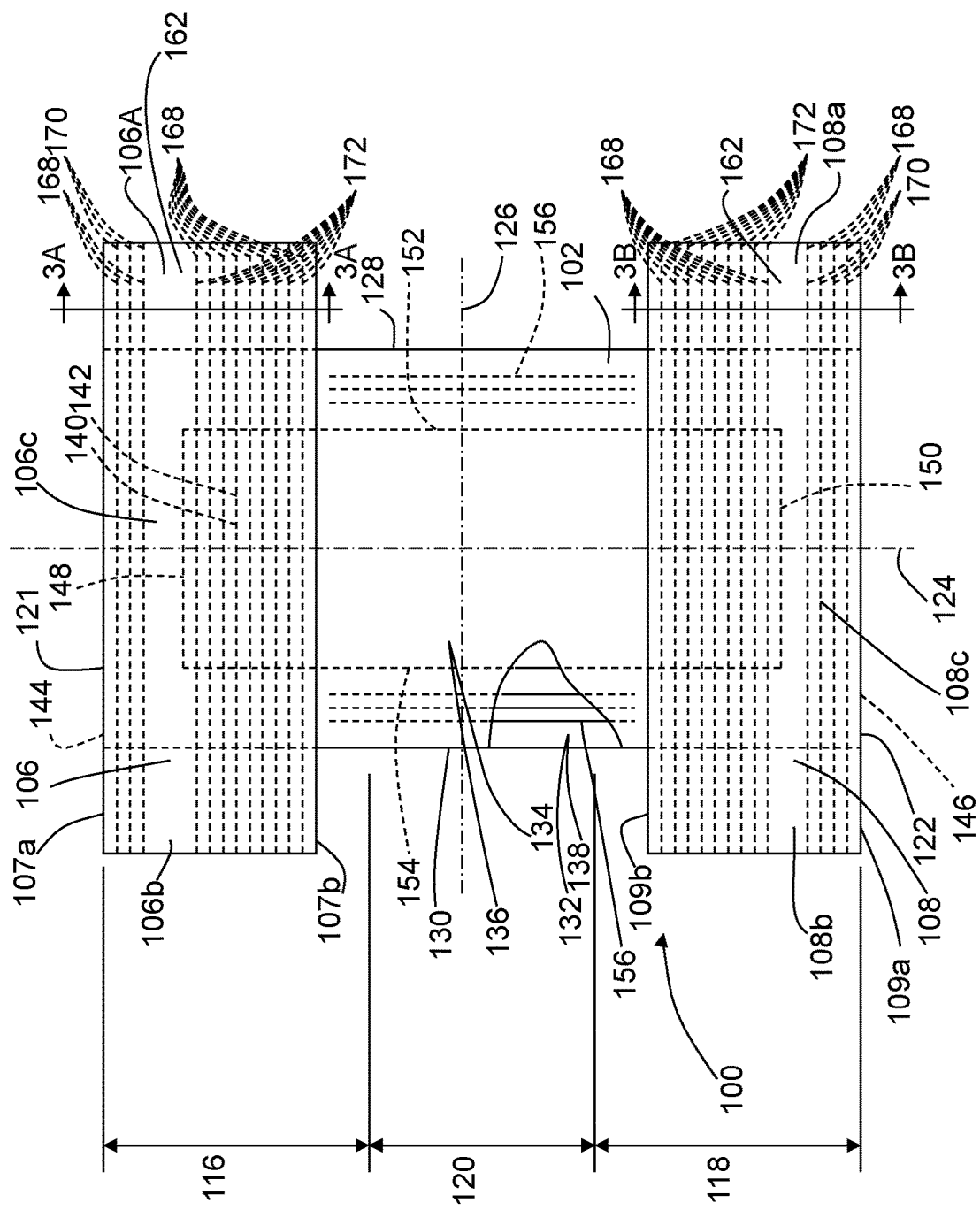
FIG. 2B is a partially cut away plan view of a second embodiment of a diaper pant.

It is to be appreciated that the chassis 102 and elastic belts 106, 108 may be configured in different ways other than as depicted in FIG. 2A. For example, FIG. 2B shows a plan view of a diaper pant 100 having the same components as described above with reference to FIG. 2A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

Figure 4:
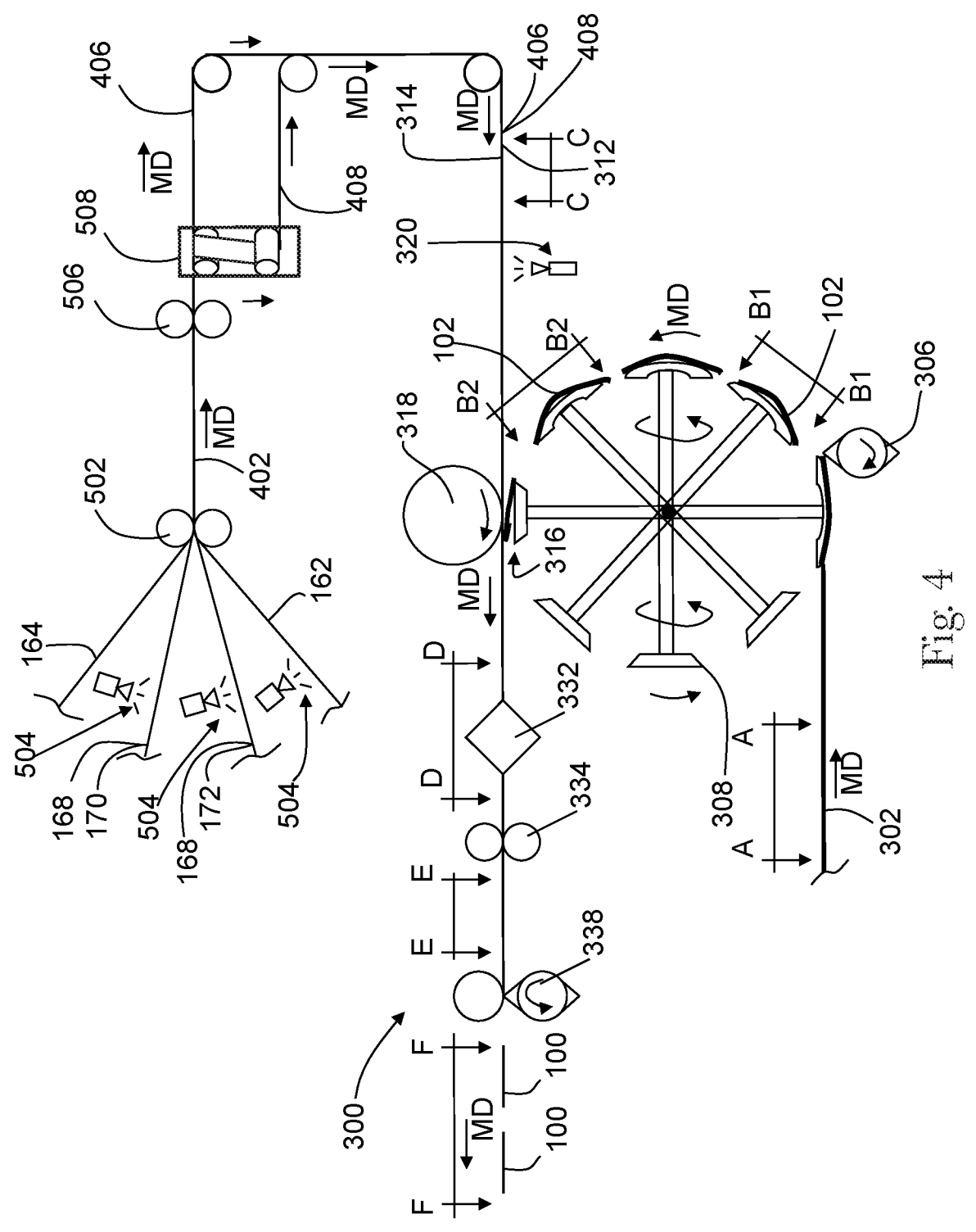

As previously mentioned, the apparatuses and methods according to the present disclosure may be utilized to assemble various components of pre-fastened, refastenable pant diapers 100. For example, FIG. 4 shows a schematic view of a converting apparatus 300 adapted to manufacture pant diapers 100. The method of operation of the converting apparatus 300 may be described with reference to the various components of pant diapers 100 described above and shown in FIGS. 1 and 2A. Although the following methods are provided in the context of the diaper 100 shown in FIGS. 1 and 2A, it is to be appreciated that various embodiments of diaper pants can be manufactured according to the methods disclosed herein, such as for example, the absorbent articles disclosed in U.S. Pat. No. 7,569,039; U.S. Patent Publication Nos. 2005/0107764 A1, 2012/0061016 A1, and 2012/0061015 A1, which are all hereby incorporated by reference herein.

As described in more detail below, the converting apparatus 300 shown in FIG. 4 operates to advance discrete chassis 102 along a machine direction MD such that the lateral axis of each chassis 102 is parallel with the machine direction, and wherein the chassis 102 are spaced apart from each other along the machine direction. Opposing waist regions 116, 118 of the spaced apart chassis 102 are then connected with continuous lengths of advancing first and second elastic belt laminates 406, 408. The chassis 102 are then folded along the lateral axis to bring the first and second elastic belt laminates 406, 408 into a facing relationship, and the first and second elastic belt laminates are bonded together with bonds 336. As discussed in more detail below, the first and second elastic belt laminates may be bonded together with adjacent bonds 336a, 336b intermittently spaced along the machine direction. Each bond 336a, 336b may be a discrete bond site extending contiguously in the cross direction across a width of the first and second elastic belt laminates. The elastic belt laminates 406, 408 are then cut in the cross direction between the adjacent bonds 336a, 336b to create discrete diapers 100, such as shown in FIG. 1.

As shown in FIG. 4, a first continuous substrate layer in the form of a continuous length of outer layer belt material 162; a second continuous substrate layer in the form of a continuous length of inner layer belt material 164; and elastics 168 are combined to form a continuous elastic laminate in the form of a belt material 402. More particularly, continuous lengths of outer layer belt material 162, inner layer belt material 164, outer elastic strands 170 and inner elastic strands 172 are advanced in a machine direction MD and combined at nip rolls 502 to form a continuous length of belt material 402. Before entering the nip rolls 502, the outer elastic strands 170 and inner elastic strands 172 are stretched in the machine direction MD. In addition, adhesive 504 may be applied to the elastic strands 170, 172 as well as either or both of the continuous lengths of outer layer belt material 162 and inner layer belt material 164 before entering nip rolls 502. Further, adhesive 504 may be applied intermittently along the lengths of the inner elastic strands 172 and/or intermittently along the length of either or both of the continuous lengths of outer layer belt material 162 and inner layer belt material 164 before entering nip rolls 502. As such, the inner elastic strands 172 may be intermittently bonded to either or both of the continuous lengths of outer layer belt material 162 and inner layer belt material 164 along the machine direction MD. Thus, the belt material 402 may include non-bonded regions intermittently spaced between bonded regions along the machine direction MD, wherein the inner elastic strands 172 are not bonded to either the outer layer belt material 162 or inner layer belt material 164 in the non-bonded regions. And the inner elastic strands 172 are bonded to the outer layer belt material 162 and/or inner layer belt material 164 in the bonded regions. Although FIG. 4 shows an embodiment wherein the belt material 402 is formed by combining continuous lengths of outer layer belt material 162 and inner layer belt material 164 with elastic strands 168, it is to be appreciated the belt material 402 can be formed in various ways, such as disclosed in U.S. Pat. No. 8,440,043 and U.S. patent application Ser. Nos. 13/434,984; 13/435,036; 13/435,063; 13/435,247; and 13/435,503 all filed on Mar. 30, 2012.

Referring back to FIG. 4, from the nip rolls 502 the continuous length of belt material 402 advances in the machine direction MD to a cutter 506 that cuts the belt material 402 into two continuous belt substrates, referred to as a first belt substrate 406 and a second belt substrate 408. The cutter 506 may be configured in various ways. For example, in some embodiments the cutter 506 may be a slitter or a die cutter that separates the belt material into two continuous belt substrates with either a straight line cut and/or a curved line cut. The cutter 506 may also be configured as a perforator that perforates the belt material with a line of weakness and wherein the belt material is separated along the line of weakness in a later step. From the cutter 506, the first and second belt substrates 406, 408 advance through a diverter 508 that separates the first and second belt substrates from each other in the cross direction CD, such as shown in FIG. 5B. The elastic strands 170, 172, and thus, the continuous length of first and second belt substrates 406, 408 are maintained in a stretched condition while advancing along the machine direction MD. It is to be appreciated that the diverter 508 may be configured in various ways. For example, in some embodiments, the diverter 508 may include turn bars angled at 45 degrees or some other angle with respect to the machine direction. In some embodiments, the diverter may include cambered rollers. Other embodiments may include diverters in the form of a pivot table, such as, for example, the FIFE-500 Web Guiding System, by Maxcess-FIFE Corporation. The diverter may also include instrumentation and web edge control features that allow for precise active control of the substrate positions. As discussed in more detail below, the first and second belt substrates 406, 408 advance from the diverter 508 to a nip 316 between the carrier apparatus 308 and a roll 318.

As shown in FIGS. 4 and 5A, a continuous length of chassis assemblies 302 are advanced in a machine direction MD to a carrier apparatus 308 and cut into discrete chassis 102 with knife roll 306. The continuous length of chassis assemblies may include absorbent assemblies 140 sandwiched between topsheet material 138 and backsheet material 136, leg elastics, barrier leg cuffs and the like. As shown in FIG. 5A, portion of the chassis assembly is cut-away to show a portion of the topsheet material 138 and an absorbent assembly 140.

After the discrete absorbent chassis 102 are cut by the knife roll 306, the carrier apparatus 308 rotates and advances the discrete chassis 102 in the machine direction MD in the orientation shown in FIG. 5B1, wherein the longitudinal axis 124 of the chassis 102 is generally parallel with the machine direction MD. While the chassis 102 shown in FIG. 5B1 is shown with the second laterally extending end edge 146 as a leading edge and the first laterally extending end edge 144 as the trailing edge, it is to be appreciated that in other embodiments, the chassis 102 may be advanced in other orientations. For example, the chassis may be oriented such that the second laterally extending end edge 146 is a trailing edge and the first laterally extending end edge 144 is a leading edge. The carrier apparatus 308 also rotates while at the same time changing the orientation of the advancing chassis 102. The carrier apparatus 308 may also change the speed at which the chassis 102 advances in the machine direction MD. It is to be appreciated that various forms of carrier apparatuses may be used with the methods herein, such as for example, the carrier apparatuses disclosed in U.S. Pat. No. 7,587,966 and U.S. patent application Ser. Nos. 13/447,585; 13/447,568; 13/447,544; and Ser. No. 13/447,531. FIG. 5B2 shows the orientation of the chassis 102 on the carrier apparatus 308 while advancing in the machine direction. More particularly, FIG. 5B2 shows the chassis 102 with the lateral axis 126 of the chassis 102 generally parallel with the machine direction MD, and wherein the second longitudinal side edge 130 is the leading edge and the first longitudinal side edge 128 is the trailing edge.

As discussed below with reference to FIGS. 4, 5C, 5D, 5E, and 5F, the chassis 102 are transferred from the carrier apparatus 308 and combined with advancing, continuous lengths of belt laminates 406, 408, which are subsequently cut to form first and second elastic belts 106, 108 on diapers 100.

With reference to FIGS. 4 and 5C, the chassis 102 are transferred from the carrier apparatus 308 to a nip 316 between the carrier apparatus 308 and a roll 318 where the chassis 102 is combined with continuous lengths of advancing front belt 406 and back belt 408 substrate material. The front belt laminate material 406 and the back belt laminate material 408 each define a wearer facing surface 312 and an opposing garment facing surface 314. The wearer facing surface 312 of the first belt laminate 406 may be combined with the garment facing surface 134 of the chassis 102 along the first waist region 116, and the wearer facing surface 312 of the second belt laminate 408 may be combined with the garment facing surface 134 of the chassis 102 along the second waist region 118. As shown in FIG. 4, adhesive 320 may be intermittently applied to the wearer facing surface 312 of the first and second belt laminates 406, 408 before combining with the discrete chassis 102 at the nip 316 between roll 318 and the carrier apparatus 308.

With reference to FIGS. 4 and 5D, a continuous length of absorbent articles 400 are defined by multiple discrete chassis 102 spaced from each other along the machine direction MD and connected with each other by the second belt laminate 408 and the first belt laminate 406. As shown in FIG. 4, the continuous length of absorbent articles 400 advances from the nip 316 to a folding apparatus 332. At the folding apparatus 332, each chassis 102 is folded in the cross direction CD along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second belt laminate 408 extending between each chassis 102 in a facing relationship with the wearer facing surface 312 of the first belt laminate 406 extending between each chassis 102. As shown in FIGS. 4, 5D, and 5E, the folded discrete chassis 102 connected with the first and second belt laminates 406, 408 are advanced from the folding apparatus 332 to a bonder apparatus 334. The bonder apparatus 334 operates to bond an overlap area 362, thus creating discrete bonds 336a, 336b. The overlap area 362 includes a portion of the second belt laminate 408 extending between each chassis 102 and a portion of the first belt laminate 406 extending between each chassis 102. As shown in FIGS. 4 and 5F, a continuous length of absorbent articles are advanced from the bonder 334 to a knife roll 338 where the first belt laminate 406 and the second belt laminate 408 are cut along the cross direction between adjacent bonds 336a, 336b to create discrete absorbent articles 100. As such, bond 336a may correspond with and form a first side seam 178 on an absorbent article 100, and the bond 336b may correspond with and form a second side seam 180 on a subsequently advancing absorbent article.

Although the absorbent article is described as having a first and second belt laminate, it is to be appreciated that the absorbent article may have only one belt laminate. Further, it is to be appreciated that the chassis and belt laminate of the absorbent article may be one continuous substrate such that the overlap area is formed from the same substrate. As such, the bonder apparatus may operate to bond a continuous substrate at an overlap area to form one or more discrete bonds.

Figure 6B:
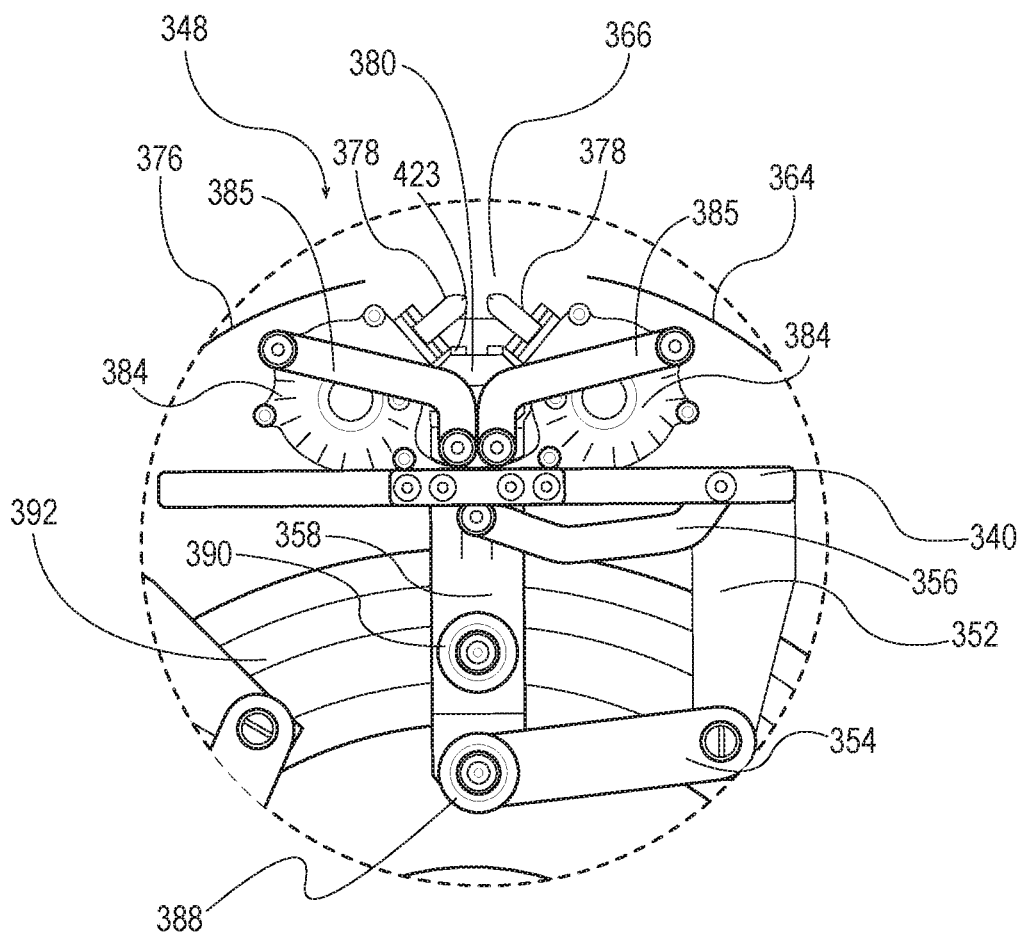
FIG. 6B is an elevation view of the seamer station of FIG. 6A.

As previously mentioned, with reference to FIG. 4, the converting apparatus may include a bonder apparatus 334 to create bonds 336a, 336b. As discussed in more detail below, the bonder apparatus 334 may include a press member 380 having a pattern surface 423 adapted to bond first and second elastic belt laminates together with bonds 336. In some embodiments, the press member 380 may include two pattern surfaces 423a, 423b, wherein a first pattern surface 423a is adapted to form a first bond 336a, and a second pattern surface 423b is adapted to form a second bond 336b. It is to be appreciated that pattern surfaces herein may be configured to operate with various types of bonder apparatuses. For example, FIG. 6A shows a detailed schematic side view of an embodiment of a bonder apparatus 334 that may be utilized with the methods and apparatuses herein. As shown in FIG. 6A, the bonder apparatus 334 may include a drum 364 and an anvil roll 368 located adjacent the drum 364. The anvil roll 368 includes an outer circumferential surface 370 and is adapted to rotate about an axis of rotation 372. The drum 364 may also include an outer circumferential surface 376 and is adapted to rotate about an axis of rotation 374. The drum 364 may also include one or more drum apertures 366 in the outer circumferential surface 376. In addition, a plurality of seaming stations 348 are positioned radially inward from the outer circumferential surface 376 and the drum apertures 366. As discussed in more detail below, with reference to FIG. 6B, each seaming station 348 may include a fluid nozzle 378 and a press member 380. Although the drum 364 shown in FIG. 6A includes six seaming stations 348, it is to be appreciated that the drum 364 may be configured to include more or less than six seaming stations 348.

During operation, the drum 364 may rotate about the axis of rotation 374 and the anvil roll 368 may rotate about the axis of rotation 372 in the directions shown in FIG. 6A. A continuous length of absorbent articles 400 may advance in machine direction MD onto the outer circumferential surface 376, wherein the first belt laminate 406 is positioned between the second belt laminate 408 and the outer circumferential surface 376. As the drum 364 rotates, fluid nozzles 378 of a seaming station 348 move radially outward toward the drum aperture 366 in the outer circumferential surface 376 as shown in FIG. 6B. In addition, a fluid is heated to a temperature sufficient to at least partially melt the overlap area 362. The fluid nozzles direct a jet of the heated fluid through the drum aperture 366 and onto an overlap area 362 of the first and second substrates 406, 408, which partially melts the overlap area 362. As the drum 364 continues to rotate, the fluid nozzles retract radially inward from the drum aperture 366, and a press member 380 then shifts radially outward through the drum aperture 366. The pattern surface 423 of the press member 380 then compresses the partially melted overlap area 362 against the outer circumferential surface 370 of the anvil roll 368, creating one or more discrete bonds 336 between the first and second belt laminates 406, 408. As the drum 364 continues to rotate, the press member 380 retracts radially inward from the drum aperture 366.

Figure 7:
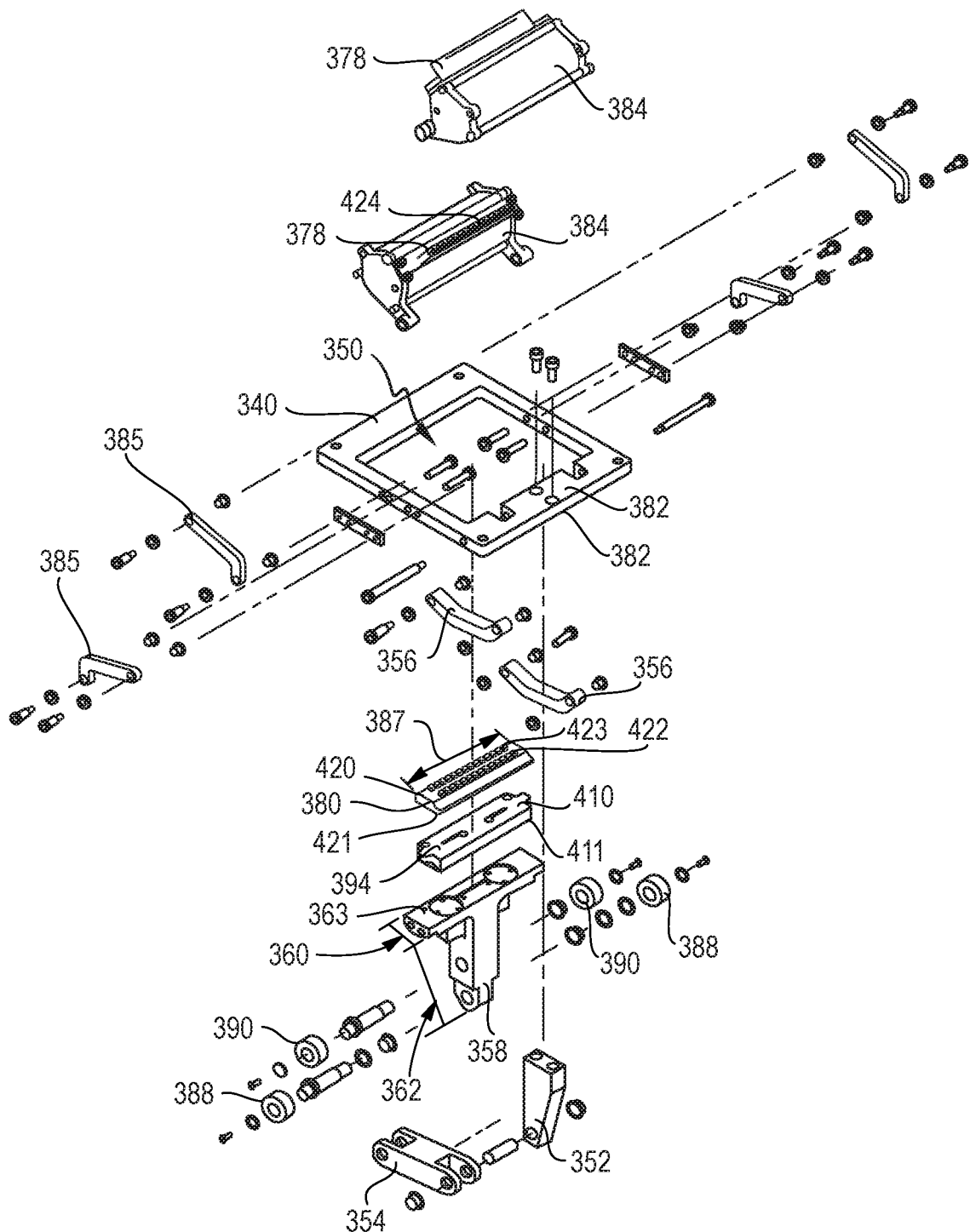
FIG. 7 is a detailed, exploded view of an embodiment of a seaming apparatus.

As previously mentioned, each seaming station of the drum may include a fluid nozzle 378 and a press member 380. FIG. 7 shows a detailed exploded view of an embodiment of a seaming station 348. As shown in FIG. 7, the seaming station 348 includes a base member 340 that is immovably connected with and rotates with the drum. The base member 340 is substantially square shaped and is defined by a base member top surface 382 and a base member bottom surface 383. The base member 340 includes a base aperture 350 extending through the base member top and bottom surfaces 382, 383 such that a fluid nozzle 384 and press member 380 may extend through the base aperture 350. Moreover, the base member bottom surface 383 is immovably connected with a base link 352. As discussed below, one end of the base link 352 is connected to the base member bottom surface 383, and another end of the base link 352 is operatively connected to a first shifting link 354.

With continued reference to FIG. 7, the seaming station 348 also includes a cam follower member 358 and first and second sets of cam rollers 388, 390 rollingly connected with the cam follower member 358. The cam follower member 358 is substantially T-shaped, and is defined by a cam follower member first portion 360, a cam follower member second portion 362, and a cam follower member top face 363. The cam follower member first portion 360 is operatively connected with the first shifting link 354 and the first set of cam rollers 388 at the same position on the cam follower member 358. Furthermore, the second set of cam rollers 390 is operatively connected to the cam follower member second portion 360 at a position radially outboard from the first set of cam rollers 388. Also operatively connected to the cam follower member 358 is a set of second shifting links 356. The set of second shifting links 356 operatively connects the base member 340 to the cam follower member first portion 360 at a position relatively outboard of the second set of cam rollers 390.

As shown in FIGS. 6A1 and 6B, the first and second set of cam rollers 388, 390 are configured to roll along a stationary cam track as the drum 364 rotates. The stationary cam track 392 surrounds the axis of rotation 374 and is defined by an inner circumferential surface 395 and a radius R that extends from the inner circumferential surface 395 of the stationary cam track 392 to the axis of rotation 374 as shown in FIG. 6A1. In some embodiments, the stationary cam track 392 may include various curved and/or straight regions such that the stationary cam track 392 is defined by relatively longer and shorter radii R at different points along the inner circumferential surface 395 of the stationary cam track 392. First and second sets of cam rollers 388, 390 roll on the stationary cam track 392 as the drum 364 rotates. The first, second, and third shifting links 354, 356, 385 pivot where the radius R of the stationary cam track 392 increases or decreases as the first and second set of cam rollers 388, 390 roll along the stationary cam track 392. At the same time, in regions where the stationary cam track 392 is defined by relatively longer radii, R, the cam follower member 385 shifts radially outward through the base aperture. Whereas, in regions where the stationary cam track 392 is defined by relatively shorter radii, R, the cam follower member shifts radially inward through the base aperture. It is to be appreciated that the cam track 392 may be configured to have various other shapes and sizes.

As shown FIG. 7, the seaming station 348 may also include two heating apparatuses 384. As discussed in more detail below, each heating apparatus 384 provides a pressurized fluid source for delivery of heated, pressurized fluid, such as air for example, to the fluid nozzle 378. In some embodiments, a valve may control egress of the fluid from the heating apparatus 384 and into a fluid nozzle 378. Each heating apparatus 384 is operatively connected to the base member 340 by a set of third shifting links 385. Each third shifting link 385 is operatively connected to one end of one heating apparatus 384 and also to the cam follower member second portion 365.

With continued reference to FIG. 7 and as discussed above, the seaming station may also include a fluid nozzle 378. The fluid nozzle 378 may include one or more fluid orifices 424 where the heated, pressurized fluid is released from the fluid nozzle 378. Each heating apparatus 384 is immovably connected with a separate fluid nozzle 378. As shown in FIG. 7, the fluid orifices 424 may be circular and may extend in a row along the fluid nozzle 378. The heated fluid may include ambient air or other gases. It is to be appreciated that the fluid may be heated to various temperatures and pressurized to various pressures. For example, in some embodiments, the fluid may be heated up to a temperature ranging from the lower melting point of first and second belt laminates minus 30° C. to the lower melting point of the first and second belt laminates plus 100° C. In some embodiments, the fluid pressure may range from $0.1 \times 10^5$ Newtons per square meter to $1 \times 10^6$ Newtons per square meter. In some embodiments, the heated fluid may be directed toward at least one of the first and second belt laminates for a time interval ranging from 10 to 1000 milliseconds or greater. Shorter or greater time intervals may be used.

With reference to FIGS. 7 and 8, the seaming station 348 may further include a spring member 394. The spring member 394 may be substantially U-shaped and defined by a spring member top face 410, a spring member bottom face 411, and a spring member side opening 412. As shown in FIG. 7, the spring member bottom face 411 is fixedly connected to the cam follower member top face 363. The spring member 394 may extend along the entirety of the cam follower member top face 363. As discussed in further detail below, the spring member side opening 412 allows the spring member 394 to flex as a press member 380 compresses the partially melted overlap area against the anvil roll outer circumferential surface.

Figure 7B:
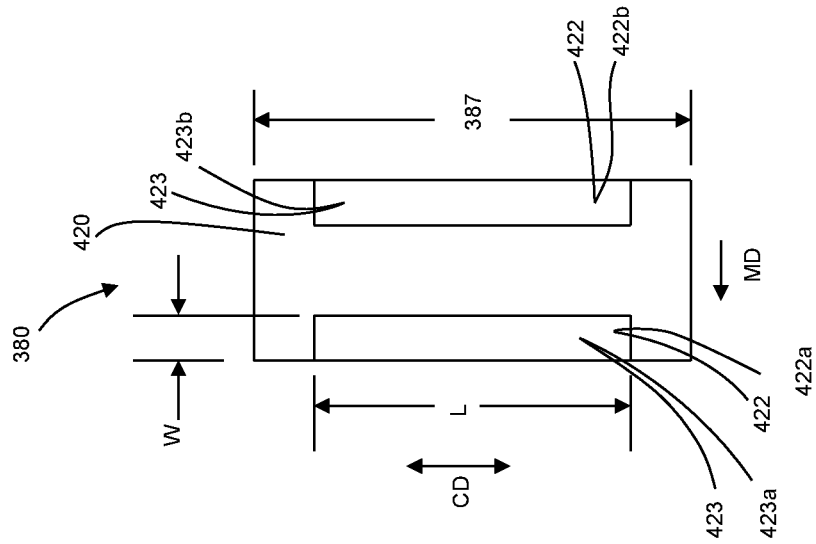
FIG. 7B is a top side view of the press member of FIG. 7A.
Figure 7A:
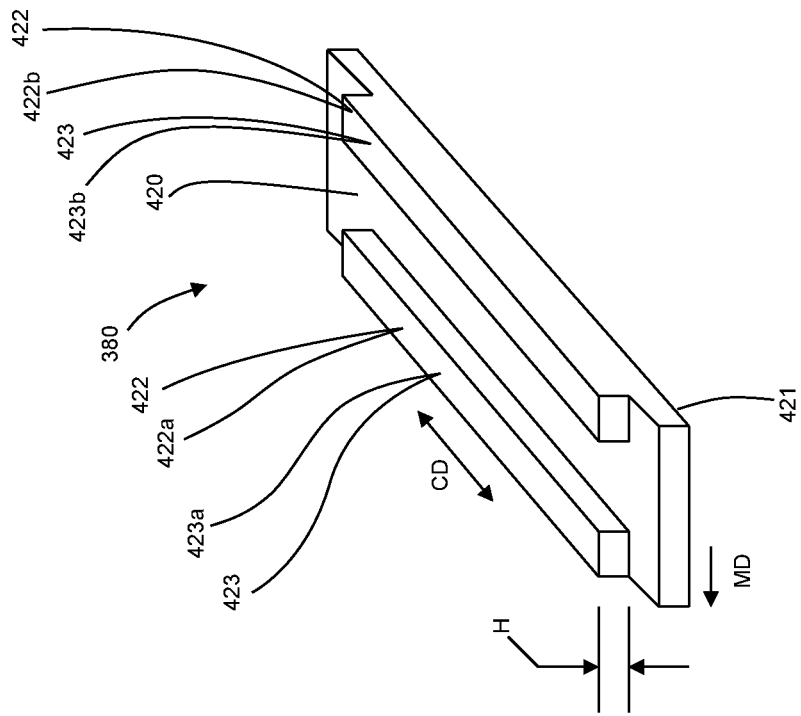
FIG. 7A is a detailed, perspective view of a press member of FIG. 7.

As previously discussed, the seaming station may also include a press member 380 to compress the partially melted overlap area against the outer circumferential surface of the anvil roll, such as shown in FIGS. 7, 7A, and 7B. The press member 380 may be substantially rectangular in shape and defined by a press member top face 420, a press member bottom face 421, and a press member length 387. The press member 380 may include one or more projections 422 extending outwardly from the press member top face 420 to define pattern surfaces 423. The press member 421 bottom face is immovably connected to the spring member top face 410. The press member 380 may extend along the entirety of the spring member top face 410.

As shown in FIGS. 7A and 7B, the press member may include two projections 422a, 422b defining two pattern surfaces 423a, 423b, respectively, spaced apart from each other along the machine direction MD. As discussed in more detail below, the first pattern surface 423a may be adapted to form a first bond 336a, and the second pattern surface 423b is adapted to form a second bond 336b. The pattern surfaces 423a, 423b may each define a width W extending in the machine direction and a length L extending in the cross direction CD. In some embodiments, the projections may have a width W in the range of about 2 millimeters to about 10 millimeters, or between about 4 millimeters to about 6 millimeters. As shown in FIGS. 7A and 7B, the length L of the pattern surfaces 423 may be less than the length 387 of the top face 410 of the press member 380. It is to be appreciated that in some embodiments, the length L of the pattern surfaces 423 may be the same as or more than the length 387 of the top face 410 of the press member 380. Although the pattern surfaces 423 shown in FIGS. 7A and 7B are rectangular-shaped, it is to be appreciated that the pattern surfaces 423 may have various other shapes. For example, the pattern surfaces 423 may extend in the cross direction along a curved path, so as to define an arc shape or an S-shape. In addition, the pattern surfaces 423 may have a constant width W or a width W that varies along the length L. The pattern surfaces 423a, 423b may also define the same or different shapes. It is also to be appreciated that the press member 380 may include more or less than two projections 422. The projections 422 may extend outwardly from the press member top face 420 to define a height, H. In some embodiments, the height may be in the range of about 0.5 millimeters to about 5 millimeters. It is also to be appreciated that the height H may be constant or may vary along the width W and/or length L. The pattern surfaces of the press member may have a smooth surface such that the bonds will be smooth. In some embodiments, the pattern surfaces of the press member may have a rough surface that result in bonds having roughened or patterned a texture.

As discussed in more detail below, the seaming stations 348 may be adapted operate in first and second configurations as the drum 346 rotates while bonding first and second elastic belt laminates together with bonds 336. For example, as shown in FIGS. 8 and 9, when the seaming station 348 is in a first configuration, the fluid nozzles 378 are positioned radially outward near the drum aperture 366 and drum outer circumferential surface 376, while the press member 380 is positioned radially inward, away from the drum aperture 366 and the drum outer circumferential surface 376. In addition, the fluid nozzles 378 are positioned at the same circumferential location as the projections 422 of the press member 380, such that the heated fluid is directed to the same locations on the overlap area that will subsequently be compressed by the press member 380. As shown in FIG. 10, when the seaming station 348 is in a second configuration, the press member 380 extends through the drum aperture beyond the outer circumferential surface, and the heating apparatuses 384 are positioned radially inward, away from the drum aperture 366. In addition, and the fluid nozzles 378 are located on either side of the cam follower member adjacent to the drum outer circumferential surface 366.

FIG. 11 shows a schematic view of the bonder apparatus 334 highlighting examples of various configurations of a seaming station 348 during rotation of a drum 364. As shown in FIG. 11, an individual seaming station may be in a first configuration 430 for approximately 180 degrees rotation around the drum 364. Next, each seaming station may transition through a shifting configuration 432, where the seaming station shifts from a first configuration to a second configuration for approximately sixty degrees rotation around the drum 364. Each seaming station may then be in a second configuration 434 for approximately sixty degrees rotation around the drum 364. And lastly, each seaming station may transition through a resetting configuration 436, where the seaming station shifts from a second configuration to a first configuration for approximately sixty degrees rotation around the drum 364. It is to be appreciated that the seaming station may be in each configuration for greater or less degrees of rotation around the drum 364 than is shown in FIG. 11.

To provide additional context to the above discussion, the following provides a specific description of an example implementation of the apparatuses and processes herein used to bond elastic substrates together. As shown in FIG. 6A, a continuous length of absorbent articles 400 advance in the machine direction MD onto the outer circumferential surface 376 as the drum 364 is rotating about the axis of rotation 374. The first belt laminate 406 is between the second belt laminate 408 and the drum outer circumferential surface 376. More particularly, the outer layer 162 of the first belt laminate 406 may be in direct contact with the drum outer circumferential surface 376. And the inner layer 164 of the first belt laminate 406 may be in direct contact with the inner layer 164 of the second belt laminate 408. The outer circumferential surface 376 may be moving at the same speed as the advancing absorbent articles 400 such that the position the absorbent articles 400 remains constant relative to the outer circumferential surface 376 until the absorbent articles 400 are removed from the drum 364. The overlap area 362 of the first and second belt laminate 406, 408 is positioned on the drum outer circumferential surface 376 coincident with a drum aperture 366. As mentioned above, the seaming station 348, located radially inward from the drum aperture 366, is configured to bond a portion of the overlap area 362 as the absorbent articles 400 travel along the drum 364.

The seaming station 348 is arranged in a first configuration as the absorbent articles are received on the drum 364. With reference to FIGS. 6A and 6B, the continuous length of absorbent articles 400 wrap around the drum outer circumferential surface 376 as the drum 364 rotates. At the same time, a jet of heated, pressurized fluid is directed from the heating apparatuses 384 out of the fluid nozzles 378 and onto the overlap area 376 of the first and second belt laminates 406, 408. The fluid nozzles 378 are maintained a preselected distance Y from the outer layer 162 of the first belt laminate 406 to control the pressure applied to the overlap area by the heated fluid as shown in FIG. 6B1. In some embodiments, the distance Y between the outer layer 162 of the first belt laminate 406 and the fluid nozzles 378 may be maintained within 3 mm of the preselected distance Y.

Once the overlap area is at least partially melted, the seaming station shifts to the second configuration and as the drum 364 continues to rotate. With reference to FIGS. 6A, 6A1, 6B, and 6B1, first and second sets of cam rollers 388, 390 roll on the stationary cam track 392 as the drum 364 rotates. The stationary cam track 392 remains stationary while the first and second set of cam rollers 388, 390 roll along the stationary cam track 392. As the first and second sets of cam rollers 388, 390 roll from regions where the radius R of the stationary cam track 392 is defined by relatively shorter radii R to regions where the radius R of the stationary cam track 392 is defined by relatively longer radii R, the first, second, and third shifting links 354, 356, 385 pivot. With reference to FIG. 6B, the first shifting link 354 pivots at the base link 352 and at the cam follower member 358, while the set of second shifting links 356 pivot at the cam follower member 358 and at the base member 340. At the same time, the cam follower member 358 shifts radially outward toward the drum outer circumferential surface 376. The third shifting links 385 also pivot at the cam follower member 358, causing the heating apparatuses 384 to move radially inward, away from the drum outer circumferential surface 376, and causing the fluid nozzles 378 to spread circumferentially apart from each other on either side of the press member 380. The seaming station 348 continues to shift until the first and second set of cam rollers 388, 390 roll along regions of the stationary cam track 392 where the radius R of the stationary cam track 392 remains constant, which corresponds to the second configuration of the seaming station 348. The seaming station 348 remains in the second configuration until the first and second set of cam rollers 388, 390 travel along the stationary cam track 392 to regions where the stationary cam track is defined by relatively shorter radii.

With continued reference to FIGS. 6A and 6B, while the drum 364 continues to rotate and the seaming station 348 is in the second configuration, the partially melted overlap area approaches the anvil roll 368 located adjacent the drum 364. As the absorbent articles 400 advance between the anvil roll 368 and drum 364, the projections 422a, 422b of the press member 380 extending through the drum aperture 366 compress the partially melted overlap area 362 against the outer circumferential surface 370 of the anvil roll 368. More particularly, the pattern surfaces 423a, 423b of the press member 380 are configured to contact the same locations of the overlap areas 362 that are at least partially melted by the heated fluid, thus forming discrete bond sites 336a, 336b in the overlap area, such as shown in FIG. 5E.

The spring member 394 may be used to apply a predetermined force to the overlap area between the press member 380 and the anvil roll 368. Once compressed, the absorbent articles advance from the outer circumferential surface of the drum. The drum continues to rotate and the seaming station shifts back to the first configuration in order to form discrete bond sites in a subsequent absorbent article. In some embodiments, the press member may compress the partially melted overlap area against the outer circumferential surface of the anvil roll at a pressure in the range of about $1 \times 10^5$ Newtons per square meter to about $1 \times 10^8$ Newtons per square meter. In some embodiments, the press member 366 may compress the first and second belt substrates for a time period ranging from 10 to 1000 milliseconds or greater. Shorter or greater time intervals may be used.

In accordance with the above discussion of the methods herein, it is to be appreciated that the press member 380 may be configured in various ways to bond elastic laminates together, such as the first belt laminate 406 and the second belt laminate 408. For example, FIGS. 5E and 5E1 illustrate an embodiment of bonds 336a, 336b that may be formed with the press member 380, such as described above with reference to FIGS. 7A and 7B. The first pattern surface 423a may be adapted to form the first bond 336a, and the second pattern surface 423b may be adapted to form a second bond 336b. As shown in FIGS. 5E1 and 5E2, the elastic laminates 406, 408 each include a plurality of elastic strands 168 interposed between an outer layer 162 and an inner layer 164. As previously discussed, the outer and/or inner layers 162, 164 may include nonwoven substrates. And the elastic strands 168 may be extend along the machine direction MD and may be separated from each other along the cross direction CD. In addition, the elastic laminates 406, 408 may also include outer edges 107a, 109a, respectively, and inner edges 107b, 109b extending along the machine direction. As such, the first elastic laminate 406 may define a width, W1, in the cross direction CD between the inner and outer edges 107a, 107b, and the second elastic laminate may define a width, W2, in the cross direction CD between the inner and outer edges 109a, 109b. It is to be appreciated that the widths, W1 and W2, of the elastic laminates 406, 408 may be the same or different. As discussed above with reference to FIGS. 7A and 7B, the first and/or second pattern surfaces 423a, 423b may define length, L, in the cross direction CD. As such, the bonds 336a, 336b may have corresponding lengths L extending in the cross direction CD, such as shown in FIGS. 5E3A-5E3C. It is to be appreciated that the length, L, of the pattern surfaces 423 and resulting bonds 336 may be configured in various ways in relation to the widths, W1 and W2, of the elastic laminates 406, 408. For example, in some embodiments, the length, L, may be configured to be equal to the widths, W1 and W2, of the elastic laminates 406, 408. In some embodiments, the length, L, may be configured to be greater than the widths, W1 and W2, of the elastic laminates 406, 408. In yet other embodiments, the length, L, may be configured to be greater than 30% of the widths, W1 and W2, and less than 100% of the widths, W1 and W2, of the elastic laminates 406, 408. In some embodiments, the length, L, may be configured such that the bonds 336 extend in the cross direction across a plurality of elastic strands 168, and in some configurations, extend across all the elastic strands 168 in the elastic laminates 406, 408.

As previously mentioned and as shown in FIGS. 5E3A-5E3C, during the bonding operation, when the elastic laminates 406, 408 are compressed between the pattern surfaces 423 and the anvil roll 368, partially melted portions 361 (represented by cross-hatched areas) of the outer layers 162 and inner layers 164 of both laminates 406, 408 are bonded together with each other and the elastic strands 168 to form the bonds 336. It is to be appreciated that the elastic strands 168 may be arranged in various ways inside the bonds 336. For example, FIG. 5E3A shows the elastic strands 168 from each laminate 406, 408 overlap with each other through the thickness of the bonds 336. In another example, FIG. 5E3B shows the elastic strands 168 from each laminate 406, 408 partially overlapping and partially interposed with each other through the thickness of the bonds 336. And in yet another example, FIG. 5E3C shows adjacent elastic strands 168 from each laminate 406, 408 interposed with each other through the thickness of the bonds 336. As such, the thickness of the bond 336 may be relatively smaller when the elastic strands 168 are interposed such as shown FIG. 5E3C.

As previously mentioned above with reference to FIGS. 4 and 5F, once the bonds 336a, 336b are formed, the absorbent articles 400 advance in the machine direction MD to a knife roll 338 where the laminates 406, 408 are cut along the cross direction CD between the bonds 336a, 336b to create a first side seam 178 on an absorbent article 100 and a second side seam 180 on a subsequently advancing absorbent article. When the knife roll 338 cuts the laminates 406, 408, the cut ends of the stretched elastic strands 168 retract or snap back to the bonds 336a, 336b. However, the likelihood that cut ends of the retracting strands 168 may retract through the bonds 336a, 336b may be reduced, because the elastic strands 168 are bonded together with the partially melted portions 361 of the outer layers 162 and inner layers 164 of both laminates 406, 408 in the bonds 336a, 336b.

In addition, during the bonding process, the frequency at which melted material from laminates 406, 408 sticks to the pattern surfaces 423 may be reduced given the relatively large size of the pattern surfaces. Further, the pattern surfaces 423 and the anvil roll may be coated to prevent the at least partially melted overlap area from sticking to the surfaces of the press member and anvil roll. The press member and anvil roll may be coated with, for example, a plasma coating, polytetrafluoroethylene, or silicone.

As previously mentioned, it is to be appreciated that pattern surfaces herein may be configured to operate with various types of bonder apparatuses, such as disclosed in U.S. Patent Publication Nos. 2013/0213547A1 and 2013/0218116A1; and U.S. Pat. No. 6,248,195. For example, FIG. 12 shows an embodiment of a bonder apparatus 334 wherein the overlapped area 362 of the elastic laminates 406, 408 are partially melted on a heating drum 512. The laminates 406, 408 then advance to a nip 514 between a rotating anvil drum 516 and a rotating bonding drum 518, wherein press members 380 having pattern surfaces 423 on the bonding drum 518 press and bond the laminates 406, 408 together with bonds 336, such as discussed above.

As shown in FIG. 12, the heating drum 512 may include a plurality of fluid outlets 520 disposed about a periphery of the heating drum 512. In turn, the each fluid outlet 520 may be in fluid communication with a fluid chamber 522 that provides a pressurized fluid source for delivery of heated, pressurized fluid to the fluid outlets 520. A heating device 524 may also be provided for heating the fluid within the fluid chamber. In some embodiments, valves may control egress of fluid from the fluid chamber 522 and into the fluid outlets 520. The bonding drum 518 may include a plurality of press members 380 disposed about a periphery of the bonding drum 518. In operation, the laminates 406, 408 advance in the machine direction MD onto the periphery of the rotating heating drum 512. Heated fluid is delivered to the laminates 406, 408 through the plurality of fluid outlets 520 thereby at least partially melting overlapped areas laminates 406, 408. Once heated, the laminates 406, 408 advance to the nip 514 between the rotating anvil drum 516 and the rotating bonding drum 518, wherein the press members 380 compress the at least partially melted, overlapping areas 362 thereby forming bonds 336 that join the laminates 406, 408 together.

In yet other embodiments, such as shown in FIG. 13, the anvil drum 516 may be replaced by the bonding drum 518. As such, the laminates 406, 408 may advance to a nip 526 between the rotating heating drum 512 and the rotating bonding drum 518, wherein the press members 380 compress the at least partially melted, overlapping areas 362 thereby forming bonds 336 that join the laminates 406, 408 together.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling disposable pant diapers, each pant diaper comprising a chassis having a first end region and an opposing second end region separated from each other by a central region, and having a longitudinal axis and a lateral axis, the chassis comprising an absorbent core, the method comprising steps of:

advancing a continuous first substrate layer in a machine direction;

advancing a continuous second substrate layer in the machine direction;

stretching a plurality of elastic strands in the machine direction;

positioning the stretched plurality of elastic strands between the first substrate layer and the second substrate layer to form a continuous elastic laminate;

cutting the elastic laminate along the machine direction to form a first continuous elastic laminate and a second continuous elastic laminate, wherein the first continuous elastic laminate defines a width, W1, extending in the cross direction;

separating the first continuous elastic laminate and the second elastic laminate in the cross direction;

bonding a plurality of chassis with the first continuous elastic laminate and the second continuous elastic laminate;

providing a press member comprising a pattern surface that defines a length, L, that extends in a cross direction and wherein the length, L, of the pattern surface is greater than 30% of W1;
providing an anvil;
partially melting a portion of the first substrate layer and a portion of the second substrate layer;
positioning the press member such that the length, L, of the pattern surface extends across the plurality of stretched elastic strands; and
bonding the first continuous elastic laminate and the second continuous elastic laminate together with a single, contiguous bond extending in the cross direction for length L by compressing the partially melted portion of the first substrate layer, the plurality of stretched elastic strands, and the partially melted portion of the second substrate layer between the pattern surface and the anvil, and wherein adjacent elastic strands from the first continuous elastic laminate and the second continuous elastic laminate are interposed with each other through a thickness of the bond.

2. The method of claim 1, wherein the first and second substrate layers comprise nonwovens.

3. The method of claim 1, further comprising forming the plurality of chassis comprising steps of:
advancing a third continuous substrate in the machine direction;
cutting the third continuous substrate into discrete chassis, wherein each of the discrete chassis advances such that the longitudinal axis is parallel with the machine direction; and
turning each of the discrete chassis such that the lateral axis is parallel with the machine direction.

4. The method of claim 3, further comprising steps of:
folding the plurality of chassis along the lateral axis to position the first continuous elastic laminate into a facing relationship with the second continuous elastic laminate.

5. The method of claim 4, wherein the step of bonding further comprises:
forming bonds between the first continuous elastic laminate and the second continuous elastic laminate intermittently spaced along the machine direction; and
cutting the first and second continuous elastic laminates between adjacent bonds to form pant diaper side seams.

6. A method for assembling disposable pant diapers, each pant diaper comprising a chassis having a first end region and an opposing second end region separated from each other by a central region, and having a longitudinal axis and a lateral axis, the chassis comprising an absorbent core, the method comprising steps of:
advancing a continuous first elastic laminate a machine direction, the first elastic laminate comprising a first plurality of elastic strands extending between a first first substrate layer and a first second substrate layer, wherein the first elastic laminate defines a width, W1, extending in the cross direction;
advancing a continuous second elastic laminate in a machine direction, the second elastic laminate comprising a second plurality of elastic strands extending between a second first substrate layer and a second second substrate layer;
bonding a plurality of chassis with the first continuous elastic laminate and the second continuous elastic laminate;

providing a pattern surface that defines a length that extends in a cross direction;
providing an anvil;
partially melting a portion of the first first substrate layer and a portion of the first second substrate layer of the first elastic laminate and a portion of the second first substrate layer and a portion of the second second substrate layer of the second elastic laminate;
positioning the pattern surface such that the length, L, of the pattern surface extends across the plurality of first elastic strands of first elastic laminate or the plurality of second elastic strands of the second elastic laminate, wherein the length, L, of the pattern surface is at least 30% of W1; and
bonding both the partially melted portion of the first first substrate layer and the partially melted portion of the first second substrate layer with the stretched first plurality of elastic strands of the first elastic laminate and the partially melted portion of the second first substrate layer and the partially melted portion of the second second substrate layer with the second plurality of elastic strands of the second elastic laminate with a single, contiguous bond extending in the cross direction for length L by compressing the partially melted portion of the first first substrate layer, the first plurality of elastic strands, and the partially melted portion of the first second substrate layer of the first elastic laminate and the partially melted portion of the second first substrate layer and the partially melted portion of the second second substrate layer with the second plurality of elastic strands of the second elastic laminate between the pattern surface and the anvil, and wherein adjacent elastic strands from the first elastic laminate and the second elastic laminate are interposed with each other through a thickness of the bond.

7. The method of claim 6, wherein the step of bonding further comprises bonding the partially melted portion of the first second substrate layer of the first elastic laminate with the partially melted portion of the second first substrate layer of the second elastic laminate.

8. The method of claim 6, further comprising forming the plurality of chassis comprising steps of:
advancing a third continuous substrate in the machine direction;
cutting the third continuous substrate into discrete chassis, wherein each of the discrete chassis advances such that the longitudinal axis is parallel with the machine direction;
turning each of the discrete chassis such that the lateral axis is parallel with the machine direction.

9. The method of claim 8, further comprising steps of:
folding the plurality of chassis along the lateral axis to position the first continuous elastic laminate into a facing relationship with the second continuous elastic laminate.

10. The method of claim 9, wherein the step of bonding further comprises:
forming bonds between the first continuous elastic laminate and the second continuous elastic laminate intermittently spaced along the machine direction; and
cutting the first and second continuous elastic laminates between adjacent bonds to form pant diaper side seams.

* * * * *